United States Patent
Fischer et al.

(10) Patent No.: US 8,410,106 B2
(45) Date of Patent: Apr. 2, 2013

(54) HYDRAZINE-SUBSTITUTED ANTHRANILIC ACID DERIVATIVES

(75) Inventors: Rüdiger Fischer, Pulheim (DE); Heinz-Juergen Wroblowsky, Langenfeld (DE); Ernst Rudolf Gesing, Erkrath (DE); Christoph Grondal, Köln (DE); Achim Hense, Leverkusen (DE); Arnd Voerste, Köln (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/022,957

(22) Filed: Feb. 8, 2011

(65) Prior Publication Data

US 2011/0257191 A1 Oct. 20, 2011

Related U.S. Application Data

(60) Provisional application No. 61/302,651, filed on Feb. 9, 2010.

(30) Foreign Application Priority Data

Feb. 9, 2010 (EP) ..................................... 10153013

(51) Int. Cl.
*A61K 31/501* (2006.01)
*C07D 401/00* (2006.01)

(52) U.S. Cl. ................. 514/252.03; 514/381; 546/275.4; 546/272.4

(58) Field of Classification Search .............. 514/252.03, 514/381; 546/275.4, 272.4
See application file for complete search history.

(56) References Cited

U.S. PATENT DOCUMENTS

| 2007/0129407 | A1 | 6/2007 | Koyanagi et al. | |
|---|---|---|---|---|
| 2009/0181956 | A1* | 7/2009 | Ikegami et al. | ............ 514/227.8 |
| 2010/0029478 | A1 | 2/2010 | Alig et al. | |
| 2010/0048578 | A1 | 2/2010 | Jachmann et al. | |
| 2010/0048640 | A1 | 2/2010 | Jachmann et al. | |
| 2010/0113794 | A1 | 5/2010 | Nokura et al. | |

FOREIGN PATENT DOCUMENTS

| WO | WO 01/70671 | A2 | 9/2001 |
|---|---|---|---|
| WO | WO 03/015518 | A1 | 2/2003 |
| WO | WO 03/015519 | A1 | 2/2003 |
| WO | WO 03/016282 | A2 | 2/2003 |
| WO | WO 03/016283 | A1 | 2/2003 |
| WO | WO 03/016284 | A1 | 2/2003 |
| WO | WO 03/024222 | A1 | 3/2003 |
| WO | WO 03/027099 | A1 | 4/2003 |
| WO | WO 03/062226 | A1 | 7/2003 |
| WO | WO 2004/027042 | A2 | 4/2004 |
| WO | WO 2004/033468 | A1 | 4/2004 |
| WO | WO 2004/046129 | A2 | 6/2004 |
| WO | WO 2004/067528 | A1 | 8/2004 |
| WO | WO 2005/085234 | A2 | 9/2005 |
| WO | WO 2005/113506 | A1 | 12/2005 |
| WO | WO 2005/118552 | A2 | 12/2005 |
| WO | WO 2006/000336 | A2 | 1/2006 |
| WO | WO 2006/023783 | A1 | 3/2006 |
| WO | WO 2006/040113 | A2 | 4/2006 |
| WO | WO 2006/111341 | A1 | 10/2006 |
| WO | WO 2007/006670 | A1 | 1/2007 |
| WO | WO 2007/020877 | A1 | 2/2007 |
| WO | WO 2007/024833 | A1 | 3/2007 |
| WO | WO 2007/043677 | A1 | 4/2007 |
| WO | WO 2007/144100 | A1 | 12/2007 |
| WO | WO 2008/126933 | A2 | 10/2008 |

OTHER PUBLICATIONS

Hirashima, S., et al., "Benzimidazole Derivatives Bearing Substituted Biphenyls as Hepatitis C Virus NS5B RNA-Dependent RNA Polymerase Inhibitors: Structure-Activity Relationship Studies and Identification of a Potent and Highly Selective Inhibitor JTK-109," *J. Med. Chem.* 49(15):4721-4736, American Chemical Society (2006).
English language Abstract of WIPO Patent Publication No. WO 2006/000336 A2, European Patent Office, espacenet database— Worldwide (2006).
English language Abstract of WIPO Patent Publication No. WO 2007/020877 A1, European Patent Office, espacenet database— Worldwide (2007).
International Search Report for International Application No. PCT/EP2011/051665, Eurpoean Patent Office, Netherlands, mailed on Sep. 1, 2011.

* cited by examiner

*Primary Examiner* — Rei-tsang Shiao
(74) *Attorney, Agent, or Firm* — Sterne, Kessler, Goldstein & Fox P.L.L.C.

(57) ABSTRACT

The present invention constitutes new hydrazine-substituted anthranilic acid derivatives of the general formula (I),

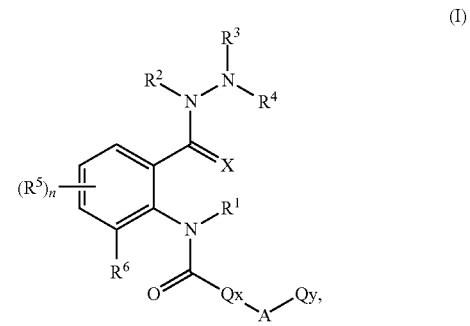

in which $R^1$, $R^2$, $R^3$, $R^4$, $R^5$, $R^6$, Qx, A, Qy and n have the definitions indicated in the description, application thereof as insecticides and acaricides for controlling animal pests, alone and in combination with further agents for activity boosting, and a number of processes for their preparation.

9 Claims, No Drawings

HYDRAZINE-SUBSTITUTED ANTHRANILIC ACID DERIVATIVES

The present invention relates to new hydrazine-substituted anthranilic acid derivatives, to their application as insecticides and acaricides for controlling animal pests, alone and in combination with further agents for activity boosting, and to a number of processes for their preparation.

Anthranilic acid derivatives having insecticidal properties have already been described in the literature, as for example in WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO2007/020877, WO 2007/144100, WO2007/043677, WO2008/126889, WO2008/126890, WO2008/126933.

In their application, however, the active ingredients already known in accordance with the specifications identified above have disadvantages in some respects, whether it be that they exhibit a narrow spectrum of application or whether it be that they do not have satisfactory insecticidal or acaricidal activity.

New hydrazine-substituted anthranilic acid derivatives have now been found which have advantages over the compounds already known, examples being better biological or environmental properties, broader application methods, an improved insecticidal or acaricidal activity, and also high compatibility with crop plants. The hydrazine-substituted anthranilic acid derivatives can be used in combination with further agents for enhancing the activity, particularly against insects which are difficult to control.

The present invention accordingly provides new hydrazine-substituted anthranilic acid derivatives of the formula (I)

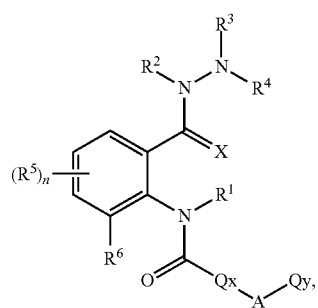

in which $R^1$ is hydrogen, amino or hydroxyl or is $C_1$-$C_6$-alkyl, $C_2$-$C_6$-alkenyl, $C_2$-$C_6$-alkynyl or $C_3$-$C_6$-cycloalkyl, each of which is optionally substituted one or more times by identical or different substituents, the substituents being selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$, $R^3$ independently of one another are hydrogen, $C_2$-$C_6$-alkoxycarbonyl, $C_2$-$C_6$-alkylcarbonyl, $C_2$-$C_6$-alkylaminocarbonyl, $C_2$-$C_6$-dialkylaminocarbonyl or are $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, or $R^2$, $R^3$ independently of one another are a phenyl ring or a 5- or 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, ($C_1$-$C_4$-alkyl)($C_1$-$C_4$-alkoxy)imino, or $R^2$ and $R^3$ may be joined to one another via two to six carbon atoms and form a ring which optionally additionally contains a further nitrogen, sulphur or oxygen atom and may optionally be substituted one to four times by $C_1$-$C_2$-alkyl, $C_1$-$C_2$-haloalkyl, halogen, cyano, amino, $C_1$-$C_2$-alkoxy or $C_1$-$C_2$-haloalkoxy, $R^4$ is a group selected from —C(=S)—$R^8$, —C(=)—$R^8$, —C(=O)—$OR^9$, —C(=S)—$OR^9$, —C(=O)—$SR^{10}$, —C(=S)—$SR^{10}$, —C(=O)—$NR^{11}R^{12}$, —C(=S)—$NR^{11}R^{12}$, —S(O)$_2$—$R^{13}$ and —S(O)$_2$—$NR^{14}R^{15}$ or $R^3$ and $R^4$ together are =$CR^{16}$ if $R^2$ and $R^3$ are not joined to one another via two to six carbon atoms and do not form a ring, $R^5$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, SF$_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two radicals $R^5$ form, via adjacent carbon atoms, a ring which is —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, or two radicals $R^5$, furthermore, form via adjacent carbon atoms the fused rings below, which are optionally substituted one or more times by identical or different substituents, the substituents being selectable independently of one another from hydrogen, cyano, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio-($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

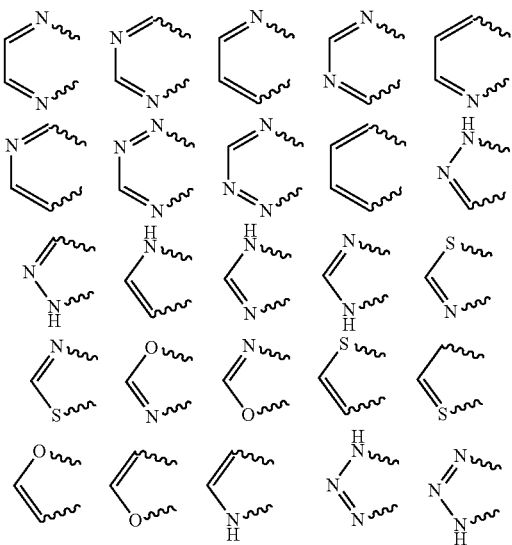

n is 0 to 3,

X is O or S, $R^6$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkyl-sulphinyl, $C_1$-$C_4$-haloalkylsulphonyl, halogen, cyano, nitro or $C_3$-$C_6$-trialkylsilyl, $Q_X$ is an aromatic or heteroaromatic 5- to 6-membered ring which is optionally substituted one or more times by identical or different substituents $R^7$ and which may contain 1-3 heteroatoms from the series N, S and O, A is optionally singly or multiply substituted —($C_1$-$C_6$-alkylene)-, —($C_1$-$C_6$-alkenylene)-, —($C_1$-$C_6$-alkynylene)-, —$R^{17}$—($C_3$-$C_6$-cycloalkyl)-$R^{17}$—, —$R^{17}$—O—$R^{17}$—, —$R^{17}$—S—$R^{17}$—, —$R^{17}$—S(=O)—$R^{17}$—, —$R^{17}$—S(=O)$_2$—$R^{17}$—, —$R^{17}$—NH—($C_1$-$C_6$-alkyl)—, —$R^{17}$—N($C_1$-$C_6$-alkyl)-$R^{17}$, —$R^{17}$—C=NO($C_1$-$C_6$-alkyl), —CH[CO$_2$($C_1$-$C_6$-alkyl)]-, —$R^{17}$—C(=O)—$R^{17}$, —$R^{17}$—C(=O)NH—$R^{17}$, $R^{17}$—C(=O)N($C_1$-$C_6$-alkyl)-$R^{17}$, —$R^{17}$—C(=O)NHNH—$R^{17}$—, —$R^{17}$—C(=O)N($C_1$-$C_6$-alkyl)-NH—$R^{17}$—, —$R^{17}$—C(=O)NHN($C_1$-$C_6$-alkyl)-$R^{17}$, —$R^{17}$—O(C=O)—$R^{17}$, —$R^{17}$—O(C=O)NH—$R^{17}$, —$R^{17}$—O(C=O)N($C_1$-$C_6$-alkyl)-$R^{17}$, —$R^{17}$—S(=O)$_2$NH—$R^{17}$, —$R^{17}$—S(=O)$_2$N($C_1$-$C_6$-alkyl)-$R^{17}$, —$R^{17}$—S(C=O)—$R^{17}$, —$R^{17}$—S(C=O)NH—$R^{17}$, —$R^{17}$—S(C=O)N($C_1$-$C_6$-alkyl)-$R^{17}$, —$R^{17}$—NHNH—$R^{17}$, —$R^{17}$—NHN($C_1$-$C_6$-alkyl)-$R^{17}$, —$R^{17}$—N($C_1$-$C_6$-alkyl)-NH—$R^{17}$, —$R^{17}$—N($C_1$-$C_6$-alkyl)-N($C_1$-$C_6$-alkyl)-$R^{17}$, —$R^{17}$—N=CH—O—$R^{17}$, —$R^{17}$—NH(C=O)O—$R^{17}$, —$R^{17}$—N($C_1$-$C_6$-alkyl)-(C=O)O—$R^{17}$, —$R^{17}$—NH(C=O)NH—$R^{17}$, —$R^{17}$—NH(C=S)NH—$R^{17}$, —$R^{17}$—NHS(=O)$_2$—$R^{17}$ or —$R^{17}$—N($C_1$-$C_6$-alkyl)S(=O)$_2$—$R^{17}$, the substituents being selectable independently of one another from halogen, cyano, nitro, hydroxyl, $C_1$-$C_6$-alkyl, $C_1$-$C_6$-alkoxy and halo-$C_1$-$C_6$-alkyl, where —($C_3$-$C_6$-cycloalkyl)- in the ring may optionally contain 1 to 2 heteroatoms selected from the series N, S and O, $R^{17}$ is linear or branched —($C_1$-$C_6$-alkylene)- or is a direct bond, and two or more radicals $R^{17}$ independently of one another are linear or branched —($C_1$-$C_6$-alkylene)- or are a direct bond, for example, $R^{17}$—O—$R^{17}$— is —($C_1$-$C_6$-alkylene)-O—$C_1$-$C_6$-alkylene)-, —($C_1$-$C_6$-alkllene)-O—, —O—($C_1$-$C_6$-alkylene)-, or —O—, $Q_Y$ is a 5- or 6-membered, partially saturated or saturated heterocyclic or heteroaromatic ring or an aromatic 8-, 9- or 10-membered fused heterobicyclic ring system or is phenyl, the ring or ring system being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, CO$_2$H, CO$_2$NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl and ($C_1$-$C_4$-alkyl)($C_1$-$C_4$-alkoxy)imino, or the substituents being selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, NO$_2$, OH, $C_1$-$C_4$-alkoxy and $C_1$-$C_4$-haloalkoxy substituents, $R^7$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_3$-$C_6$-cycloalkoxy or

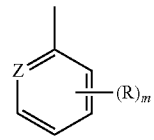

R independently at each occurrence is hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-haloalkylsulphonyl or ($C_1$-$C_4$-alkyl)$C_1$-$C_4$-alkoxyimino, m is 0 to 4, Z is N, CH, CF, CCl, CBr or CI, $R^8$ is hydrogen or is $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di($C_1$-$C_4$-alkyl)amino, $C_3$-$C_6$-cycloalkylamino, a phenyl ring or a 3- to 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, $R^8$ additionally is a phenyl ring or a 3- to 6-membered unsaturated, partially saturated or saturated heterocycle, the heteroatoms being selected from the series N, S and O, where the phenyl ring or heterocycle is optionally substituted one or more times by identical or different substituents, and where the substituents are selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, $R^9$, $R^{10}$, $R^{13}$, $R^{14}$ and $R^{15}$ independently of one another are $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di($C_1$-$C_4$-alkyl)amino, $C_3$-$C_6$-cycloalkylamino, a phenyl ring or a 3- or 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, $R^9$, $R^{10}$, $R^{13}$, $R^{14}$ and $R^{15}$ independently of one another are additionally a phenyl ring or are a 3- to 6-membered unsaturated, partially saturated or saturated heterocycle, the heteroatoms being selected from the series N, S and O, the phenyl ring or heterocycle being optionally substituted one or more times by identical or different substituents, the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, $R^{11}$, $R^{12}$ independently of one another are hydrogen or are $R^9$, $R^{16}$ is a phenyl ring or is a 5- or 6-membered heteroaromatic ring, the heteroatoms being selected from the series N, S and O, the ring being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, the compounds of the general formula (I) further comprise N-oxides and salts.

The compounds of the formula (I) may possibly be present in different polymorphic forms or as a mixture of different polymorphic forms. Both the pure polymorphs and the polymorph mixtures are provided by the invention and can be used in accordance with the invention.

The compounds of the formula (I) optionally include diastereomers or enantiomers.

A general definition of the compounds of the invention is provided by the formula (I). Preferred, more preferred and very preferred are compounds of the formula (I) in which $R^1$ preferably is hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkyl-sulphonyl-$C_1$-$C_4$-alkyl, $R^1$ more preferably is hydrogen, methyl, ethyl, cyclopropyl, cyanomethyl, methoxymethyl, methylthiomethyl, methylsulphinylmethyl or methylsulphonylmethyl, $R^1$ very preferably is hydrogen, $R^2$ and $R^3$ independently of one another preferably are hydrogen or are $C_1$-$C_6$-alkyl or $C_3$-$C_6$-cycloalkyl optionally substituted one or more times by identical or different substituents, the substituents being selectable independently of one another from halogen, cyano, $C_2$-$C_6$-alkoxycarbonyl or $C_2$-$C_6$-alkylcarbonyl, $R^2$, $R^3$ independently of one another more preferably are hydrogen, methyl, ethyl, isopropyl, tert-butyl, $R^4$ preferably is —C(=)—$R^8$, —C(=O)—$OR^9$, —C(=O)—$SR^{10}$, —C(=O)—$NR^{11}R^{12}$, —S(O)$_2$—$R^{13}$, —S(O)$_2$—$NR^{14}R^{15}$, $R^4$ more preferably is —C(=)—$R^8$ or —C(=O)—$OR^9$, $R^5$ preferably is hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio, two adjacent radicals $R^5$ likewise preferably are —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, $R^5$ more preferably is hydrogen, $C_1$-$C_4$-alkyl, $C_1$-$C_2$-haloalkyl, halogen, cyano or $C_1$-$C_2$-haloalkoxy, two adjacent radicals $R^5$ more preferably are —$(CH_2)_4$—, —$(CH=CH—)_2$—, —$O(CH_2)_2O$—, —$O(CF_2)_2O$—, —$(CH=CH—CH=N)$— or —$(CH=CH—N=CH)$—, $R^5$ very preferably is hydrogen, methyl, trifluoromethyl, cyano, fluoro, chloro, bromo, iodo or trifluoromethoxy, two adjacent radicals $R^5$ very preferably are —$(CH_2)_4$—, or —$(CH=CH—)_2$—, $R^5$ more particularly preferably is chlor, fluoro or bromo, $R^5$ additionally more particularly preferably is iodo or cyano, two adjacent radicals $R^5$ more particularly preferably are —$(CH=CH—)_2$, n preferably is 0 to 2, n more preferably is 1 or 2, n very preferably is 2, X preferably is O or S, X more preferably and very preferably is O, $R^6$ preferably is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ more preferably is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluoro, chloro, bromo, iodo, cyano, nitro or $C_3$-$C_6$-trialkylsilyl, $R^6$ very preferably is methyl, fluoro, chloro, bromo or iodo, $R^6$ more particularly preferably is methyl or chloro, $Q_X$ preferably is a heteroaromatic 5-membered ring which is optionally substituted one or more times by identical or different substituents $R^7$ and which may contain 1-3 heteroatoms from the series N, O and S, is a heteroaromatic 6-membered ring which is optionally substituted one or more times by identical or different substituents $R^7$ and which may contain 1-3 nitrogen atoms, or is phenyl, $Q_X$ more preferably is a 5- or 6-membered ring which is optionally substituted one or more times by identical or different substituents $R^7$ and is selected from the group consisting of furan, thiophene, pyrazole, triazole, imidazole, thiazole, oxazole, isoxazole, isothiazole, thiadiazole, oxadiazole, pyrrole, pyridine, pyrimidine, pyridazine and pyrazine, $Q_X$ very preferably is pyrazole, thiazole or pyrimidine which is substituted singly by the group

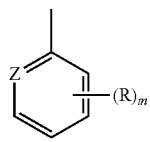

where Z, R and m may have the stated general definitions or the preferred or more preferred definitions, A preferably is optionally singly or multiply substituted —($C_1$-$C_4$-alkylene)-, —($C_1$-$C_4$-alkenylene)-, —($C_1$-$C_4$-alkynylene)-, —$R^{17}$—($C_3$-$C_6$-cycloalkyl)-$R^{17}$—, —$R^{17}$—O—$R^{17}$—, —$R^{17}$—S—$R^{17}$—, —$R^{17}$—S(=O)—$R^{17}$—, —$R^{17}$—S(=O)$_2$—$R^{17}$—, —$R^{17}$—NH—($C_1$-$C_4$-alkyl)-, —$R^{17}$—N($C_1$-$C_4$-alkyl)-$R^{17}$, —$R^{17}$—C=NO($C_1$-$C_4$-alkyl), —$R^{17}$—C(=O)—$R^{17}$, —$R^{17}$—C(=S)—$R^{17}$, —$R^{17}$—C(=O)NH—$R^{17}$, —$R^{17}$—C(=O)N($C_1$-$C_4$-alkyl)-$R^{17}$, —$R^{17}$—S(=O)$_2$NH—$R^{17}$, —$R^{17}$—S(=O)$_2$N($C_1$-$C_4$-alkyl)-$R^{17}$, —$R^{17}$—NH(C=O)O—$R^{17}$, —$R^{17}$—N($C_1$-$C_4$-alkyl)-(C=O)O—$R^{17}$, —$R^{17}$—NH(C=O)NH—$R^{17}$, —$R^{17}$—NHS(=O)$_2$—$R^{17}$ or —$R^{17}$—N($C_1$-$C_4$-alkyl)S(=O)$_2$—$R^{17}$, the substituents being selectable independently of one another from halogen, cyano, nitro, hydroxyl, $C_1$-$C_6$-alkyl, $C_1$-$C_6$-alkoxy or halo-$C_1$-$C_6$-alkyl, A more preferably is —$CH_2$—, —$CH_2O$—, —$CH_2OCH_2$—, —$CH_2S$—, —$CH_2SCH_2$—, —$CH_2N(C_1$-$C_4$-alkyl)-, —$CH_2N(C_1$-$C_4$-alkyl)CH_2$—, —CH(Hal)-, —C(Hal)$_2$-, —CH(CN)—, $CH_2(CO)$—, $CH_2(CS)$—, $CH_2CH(OH)$—, -cyclopropyl-, $CH_2(CO)CH_2$—, —CH($C_1$-$C_4$-alkyl)-, —C(di-$C_1$-$C_6$-alkyl)-, —$CH_2CH_2$—, —CH=CH—, —C≡C— or —C=NO($C_1$-$C_6$-alkyl), A very preferably is —$CH_2$—, —$CH(CH_3)$, $C(CH_3)_2$, —$CH_2CH_2$—, —CH(CN)— or —$CH_2O$—, A more particularly preferably is $CH_2$, $CH(CH_3)$ or —$CH_2O$—, $R^7$ preferably is $C_1$-$C_6$-alkyl or is the radical

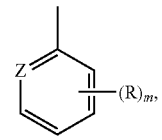

$R^7$ additionally preferably is $C_3$-$C_6$-cycloalkoxy, $R^7$ more preferably is methyl or is the radical

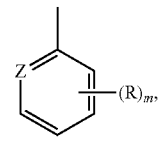

R independently at each occurrence preferably is hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkoxyimino, R independently at each occurrence more preferably is hydrogen, halogen, cyano or $C_1$-$C_4$-haloalkyl, R independently at each occurrence very preferably is fluoro, chloro or bromo, R more particularly preferably is chloro, m preferably is 1, 2 or 3, m more preferably is 1 or 2, m very preferably is 1, Z preferably is N, CH, CF, CCl, CBr or CI, Z more preferably is N, CH, CF, CCl or CBr, Z very preferably is N, CCl or CH, $R^8$ preferably is hydrogen or singly or multiply identically or differently substituted $C_1$-$C_6$-alkyl or $C_3$-$C_6$-cycloalkyl, the substituents being selectable independently of one another from halogen, cyano, a phenyl ring or a 3- or 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy or $C_1$-$C_4$-haloalkoxy, $R^8$ additionally preferably is a phenyl ring or is a 3- to 6-membered unsaturated, partially saturated or saturated heterocycle, the heteroatoms being selected from the series N, S and O, and the phenyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen or cyano, $R^8$ more preferably is hydrogen, is methyl, ethyl, isopropyl or tert-butyl optionally singly or multiply identically or differently substituted, the substituents being selectable independently of one another from halogen, cyano, phenyl or pyridyl, where phenyl or pyridyl is optionally substituted one or more times by identical or different hydrogen, trifluoromethyl, cyano, fluoro, chloro, bromo or trifluoromethoxy substituents, $R^8$ additionally more preferably is phenyl, pyridyl or is a 3- to 6-membered saturated heterocycle, containing 1-2 heteroatoms from the series N, S and O, the phenyl or pyridyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen or cyano, $R^9$, $R^{10}$, $R^{13}$, $R^{14}$ and $R^{15}$ independently of one another preferably are singly or multiply identically or differently substituted $C_1$-$C_6$-alkyl or $C_3$-$C_6$-cycloalkyl, the substituents being selectable independently of one another from halogen, cyano, a phenyl ring or a 3- to 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy or $C_1$-$C_4$-haloalkoxy, $R^9$, $R^{10}$, $R^{13}$, $R^{14}$, $R^{15}$ independently of one another additionally preferably are a phenyl ring or are a 3- to 6-membered unsaturated, partially saturated or saturated heterocycle, the heteroatoms being selected from the series N, S and O, the phenyl ring or the heterocycle being optionally substituted one or more times by identical or different substituents, and the substituents being selectable independently of one another from hydrogen, $C_1$-$C_6$-alkyl, $C_1$-$C_6$-haloalkyl, halogen or cyano, $R^9$, $R^{10}$, $R^{13}$, $R^{14}$ and $R^{15}$ independently of one another more preferably are optionally singly or multiply identically or differently substituted methyl, ethyl, isopropyl or tert-butyl, the substituents being selectable independently of one another from halogen, cyano, phenyl or pyridyl, where phenyl or pyridyl is optionally substituted one or more times by identical or different trifluoromethyl, cyano, fluoro, chloro or trifluoromethoxy substituents, $R^9$, $R^{10}$, $R^{13}$, $R^{14}$ and $R^{15}$ independently of one another additionally more preferably are phenyl, pyridyl or are a 3- to 6-membered saturated heterocycle containing 1-2 heteroatoms from the series N, S and O, the phenyl or pyridyl ring or the heterocycle optionally being substituted one or more times by identical or different substituents, and the substituents being selectable independently of one another from hydrogen, $C_1$-$C_6$-alkyl, $C_1$-$C_6$-haloalkyl, halogen or cyano, $R^{11}$ and $R^{12}$ independently of one another preferably are hydrogen or are $R^9$, $R^{16}$ preferably is a phenyl ring or is a 5- or 6-membered heteroaromatic ring where the heteroatoms are selected from the series N, S and O, the ring being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy or $C_1$-$C_4$-haloalkoxy, $R^{16}$ more preferably is phenyl, pyridyl, pyrimidinyl, furan or thiophene which is optionally substituted one or more times by identical or different substituents, the substituents being selectable independently of one another from hydrogen, trifluoromethyl, cyano, fluoro, chloro or trifluoromethoxy, $R^{17}$ preferably is linear or branched —($C_1$-$C_4$-alkylene)- or is a direct bond, $R^{17}$ more preferably is methylene, ethylene, propylene, isopropylene, n-butylene, sec-butylene, isobutylene or a direct bond, $R^{17}$ very preferably is methylene, ethylene or a direct bond, $Q_Y$ preferably is a 5- or 6-membered, partially saturated or saturated heterocyclic or heteroaromatic ring or an aromatic 8-, 9- or 10-membered fused heterobicyclic ring system, the heteroatoms being selectable from the series N, S and O, the ring or the ring system being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl and $C_1$-$C_4$-haloalkylsulphonyl, or the substituents being selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy or $C_1$-$C_4$-haloalkoxy substituents, $Q_Y$ more preferably is an optionally singly or multiply identically or differently substituted 5- or 6-membered heteroaromatic ring from the series Q-1 to Q-53, Q-58 to Q-59, Q-62 to Q-63, an aromatic 9-membered fused heterobicyclic ring system Q-54 to Q-56 or 5-membered heterocyclic ring Q-60 to Q-61, the substituents being selectable independently of one another from $C_1$-$C_4$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy or $C_1$-$C_4$-haloalkoxy substituents, $Q_Y$ very preferably is an optionally singly or multiply identically or differently substituted 5- or 6-membered heteroaromatic ring from the series Q-36 to Q-40, Q-43, Q-58 to Q-59, Q-62, Q-63, an aromatic 9-membered fused heterobicyclic ring system Q-54 to Q-56 or 5-membered heterocyclic ring Q-60 to Q-61, the substituents being selectable independently of one another from $C_1$-$C_4$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy substituents, $Q_Y$ more particularly preferably is an optionally singly or multiply identically or differently substituted heteroaromatic ring from the series Q-37, Q-38, Q-39, Q-40, Q43, Q-58, Q-59, Q-62, Q-63, or 5-membered heterocyclic ring Q-60, the substituents being selectable independently of one another from methyl, ethyl, cyclopropyl, tert-butyl, chloro, fluoro, iodo, bromo, cyano, nitro, difluoromethyl, trifluoromethyl, pentafluoroethyl, n-heptafluoropropyl or isoheptafluoropropyl, or the substituents being selectable independently of one another from phenyl or a 5- or 6-membered heteroaromatic ring, the substituents being selectable independently of one another from methyl, ethyl, cyclopropyl, tert-butyl, chloro, fluoro, iodo, bromo, cyano, nitro, difluoromethyl, trifluoromethyl, pentafluoroethyl, n-heptafluoropropyl and isoheptafluoropropyl,

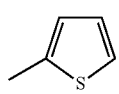
Q-1

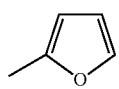
Q-2

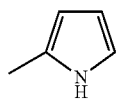
Q-3

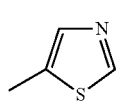
Q-4

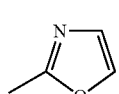
Q-5

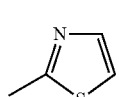
Q-6

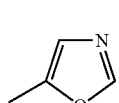
Q-7

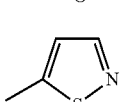
Q-8

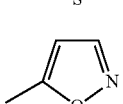
Q-9

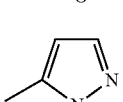
Q-10

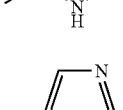
Q-11

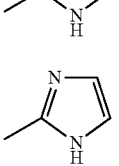
Q-12

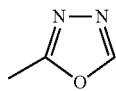
Q-13

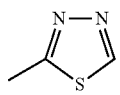
Q-14

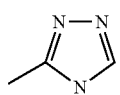
Q-15

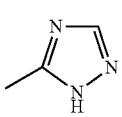
Q-16

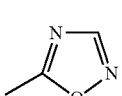
Q-17

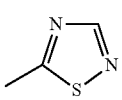
Q-18

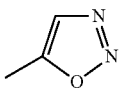
Q-19

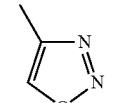
Q-20

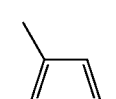
Q-21

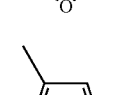
Q-22

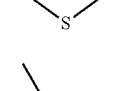
Q-23

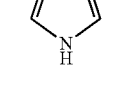
Q-24

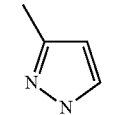
Q-25

| | |
|---|---|
| Q-26 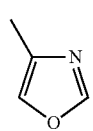 | Q-38 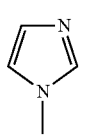 |
| Q-27 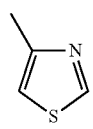 | Q-39 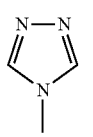 |
| Q-28 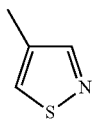 | Q-40 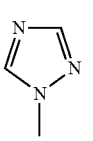 |
| Q-29 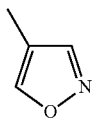 | Q-41 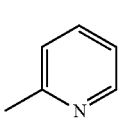 |
| Q-30 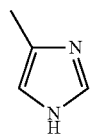 | Q-42 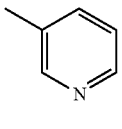 |
| Q-31 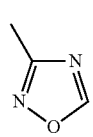 | Q-43 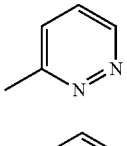 |
| Q-32 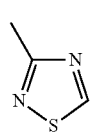 | Q-44 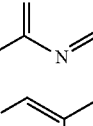 |
| Q-33 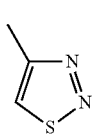 | Q-45 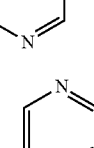 |
| Q-34 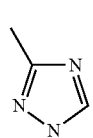 | Q-46 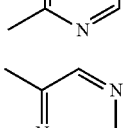 |
| Q-35 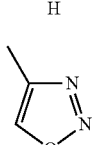 | Q-47 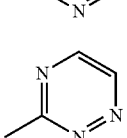 |
| Q-36 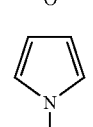 | Q-48 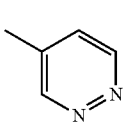 |
| Q-37 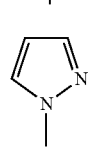 | Q-49 <br> Q-50 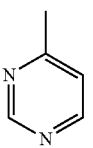 |

Q-51 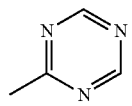

Q-52 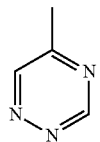

Q-53 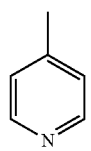

Q-54 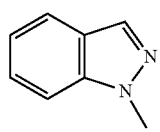

Q-55 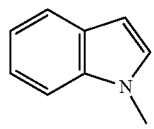

Q-56 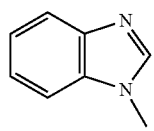

Q-57 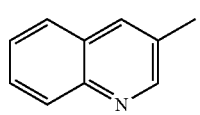

Q-58 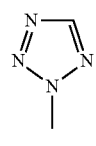

Q-59 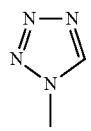

Q-60 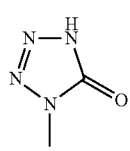

Q-61 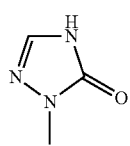

Q-62 

Q-63 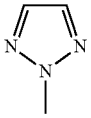

The above-recited general radical definitions and elucidations or those recited in preference ranges may be combined arbitrarily with one another, in other words including combinations between the respective ranges and preference ranges. They apply to the end products and also to the precursors and intermediates accordingly.

Preferred in accordance with the invention are the compounds of the formula (I) in which there is a combination of the definitions recited above as being preferred (preferably).

Particularly preferred in accordance with the invention are the compounds of the formula (I) in which there is a combination of the definitions recited above as being more preferred.

Very preferred in accordance with the invention are the compounds of the formula (I) in which there is a combination of the definitions recited above as being very preferred.

The compounds of the formulae (I) may be present more particularly in the form of different regioisomers: for example, in the form of mixtures of compounds with the definition Q-62 and/or Q-63, or in the form of mixtures of Q-58 and 59. The invention therefore also includes mixtures of compounds of the formulae (I) where $Q_Y$ has the definitions Q-62 and Q-63, and also Q-58 and Q-59, and the compounds may be present in different proportions. Preference in this context is given to proportions of the compounds of the formula (I) in which the radical $Q_Y$ is Q-62 or is Q-58 to compounds of the formula (I) in which the radical QY is Q-63 or is Q-59, of 60:40 to 99:1, more preferably of 70:30 to 97:3, very preferably of 80:20 to 95:5. More particularly preferred are the following proportions for a compound of the formula (I) where $Q_Y$ has the definition Q-62 or Q-58 to the compound of the formula (I) where $Q_Y$ has the definition Q-63 or Q-59: 80:20; 81:19; 82:18; 83:17; 84:16; 85:15; 86:14; 87:13; 88:12; 89:11; 90:10, 91:9; 92:8; 93:7; 96:6; 95:5.

Preparation Processes

The compounds of the general formula (I) can be obtained by procedures in which
(A) anilines of the formula (II)

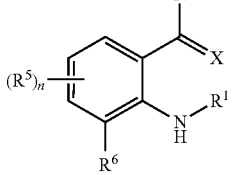
(II)

in which $R^1$, $R^2$, $R^3$, $R^4$, $R^5$, $R^6$, X and n are as defined above, are reacted for example with carbonyl chlorides of the formula (III)

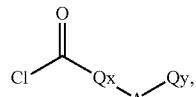
(III)

where
Qx, A and Qy are as defined above,
in the presence of an acid-binding agent; or
(B) anilines of the formula (II)

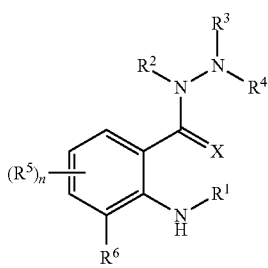
(II)

in which $R^1$, $R^2$, $R^3$, $R^4$, $R^5$, $R^6$, X and n are as defined above,
are reacted for example with a carboxylic acid of the formula (IV)

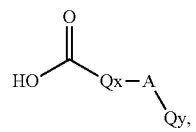
(IV)

where
Qx, A and Qy are as defined above,
in the presence of a condensing agent; or
(C) for the synthesis of anthranilimides of the formula (I) in which $R^1$ is hydrogen, for example benzoxazinones of the formula (V)

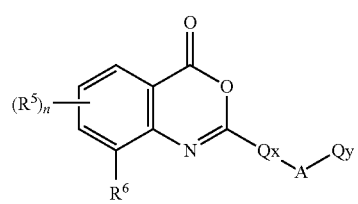
(V)

in which $R^5$, $R^6$, Qx, A, Qy and n are as defined above
are reacted with a hydrazine of the formula (VI)

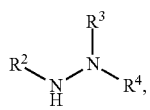
(VI)

in which $R^2$, $R^3$ and $R^4$ are as defined above,
in the presence of a diluent; or
(D) anthranilic hydrazides of the formula (VII)

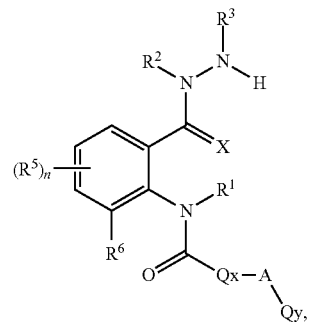
(VII)

in which $R^1$, $R^2$, $R^3$, $R^5$, $R^6$, X, n, Qx, A and Qy are as defined above,
are reacted with a unit Y—$R^4$, where $R^4$ is as defined above and Y represents a suitable leaving group such as halogen or alkoxy;
or
(E) anthranilic hydrazides of the formula (VII)

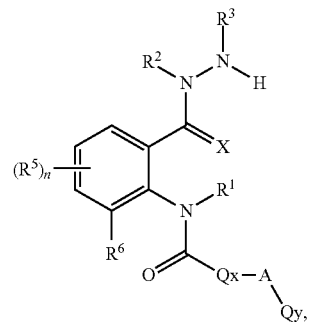
(VII)

in which $R^1$, $R^2$, $R^3$, $R^5$, $R^6$, X, n, Qx, A and Qy are as defined above,
are reacted with an acid anhydride of the general formula $(C(=O)-R^8)_2O$ or $(C(=O)-OR^9)_2O$
or with an isocyanate of the formula $O=C=NR^{11}R^{12}$,
where $R^8$, $R^9$, $R^{11}$ and $R^{12}$ are as defined above,
to give compounds of the formula (I) of the invention.
More particularly, compounds of the general formula (I) in which Qx

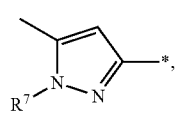

is where * marks the bond to A, can be obtained by a procedure in which
(A-1) anilines of the formula (II)

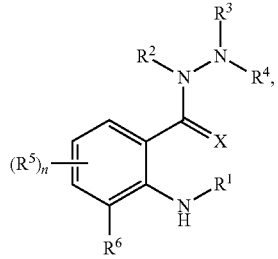

in which $R^1$, $R^2$, $R^3$, $R^4$, $R^5$, $R^6$, X and n are as defined above,
are reacted for example with carbonyl chlorides of the formula (III-1)

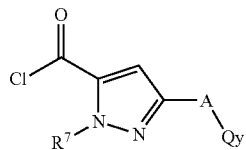

in which $R^7$, A and Qy are as defined above
in the presence of an acid-binding agent; or
(B-1) anilines of the formula (II)

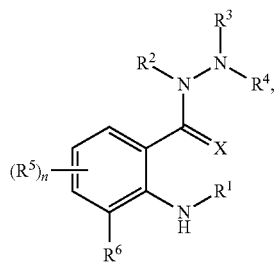

in which $R^1$, $R^2$, $R^3$, $R^4$, $R^5$, $R^6$, X and n are as defined above,
are reacted, for example, with a carboxylic acid of the formula (IV-1)

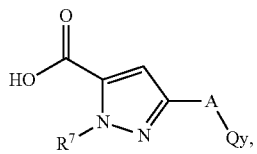

in which $R^7$, A and Qy are as defined above,
in the presence of a condensing agent; or
(C-1) for synthesis of anthranilamides of the formula (I) in which $R^1$ is hydrogen, benzoxazinones of the formula (V-1)

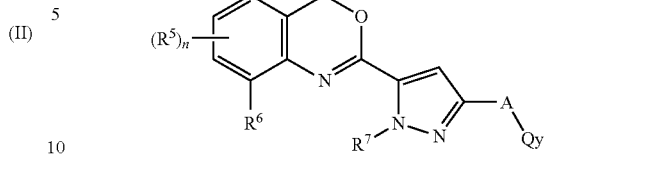

in which $R^5$, $R^6$, $R^7$, A, Qy and n are as defined above
are reacted with a hydrazine of the formula (VI)

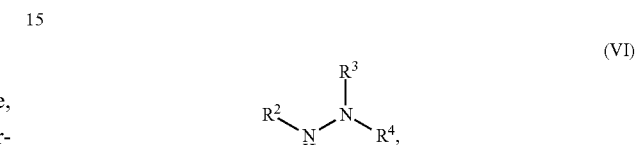

in which $R^2$, $R^3$ and $R^4$ are as defined above,
in the presence of a diluent; or
(D) anthranilic hydrazides of the formula (VII-1)

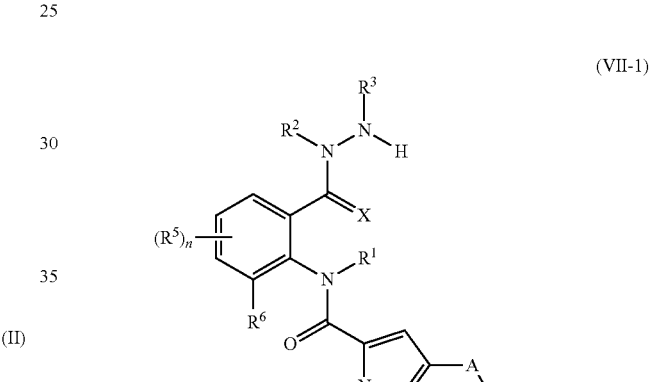

are reacted with a unit Y—$R^4$, where $R^4$ is as defined above and Y represents a suitable leaving group such as halogen or alkoxy,
or
(E) anthranilic hydrazides of the formula (VII-1)

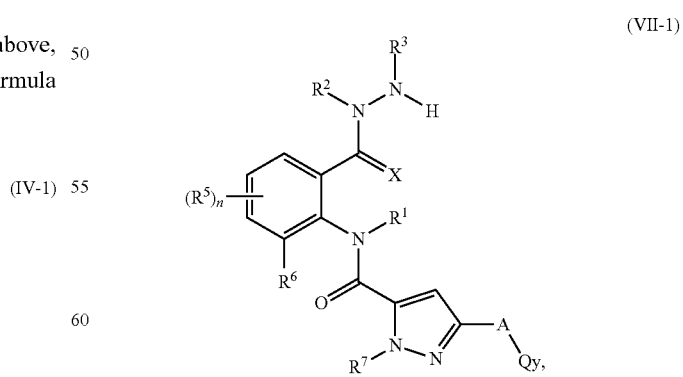

in which $R^1$, $R^2$, $R^3$, $R^5$, $R^6$, X, n, A and Qy are as defined above,
are reacted with an acid anhydride of the general formula $(C(=O)—R^8)_2O$ or $(C(=O)—OR^9)_2O$ or with an isocyanate of the formula $O=C=NR^{11}R^{12}$,
where $R^8$, $R^9$, $R^{11}$ and $R^{12}$ are as defined above,
to give compounds of the formula (I) of the invention.

More particularly, compounds of the general formula (I) in which Qx is

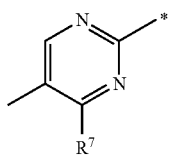

where * marks the bond to A can be prepared by a procedure in which
(B-2) anilines of the formula (II)

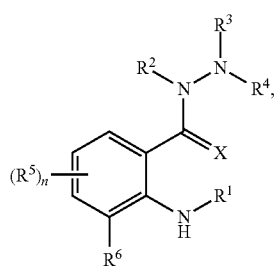
(II)

in which $R^1$, $R^2$, $R^3$, $R^4$, $R^5$, $R^6$, X and n are as defined above, are reacted, for example, with a carboxylic acid of the formula (IV-2)

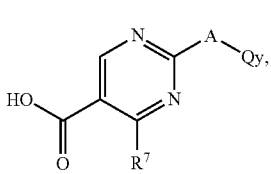
(IV-2)

in which $R^7$, A and Qy are as defined above,
in the presence of a condensing agent.

Carboxylic acids of the formula (IV-2) are new. They can be prepared by the reaction scheme below, where $R^7$, A and Qy are as defined above and R is $C_1$-$C_6$-alkyl and Hal is halogen, from compounds of the formula (VIII). Compounds of the formula (VIII) are known (e.g. J. Med. Chem. 49, 2006, 4721-4736). The reaction of (VIII) to (IX) can be carried out by known methods (e.g. WO2005/113506). The further reaction via compounds of the formula X to compounds of the formula (IV-2) can be carried out by known methods (e.g. WO2007/144100).

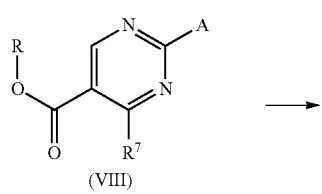
(VIII)

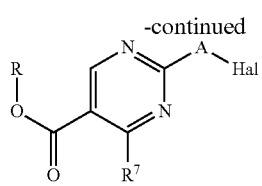
(IX)

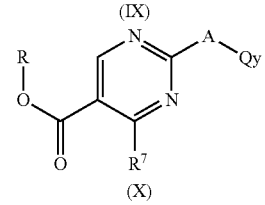
(X)

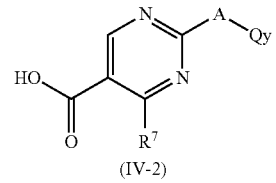
(IV-2)

More particularly, compounds of the general formula (I), in which Qx is

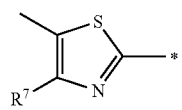

where * marks the bond to A can be prepared by a procedure in which
(B-3) anilines of the formula (II)

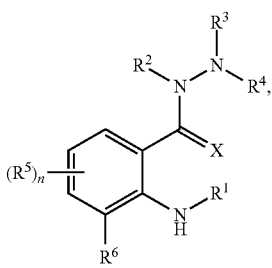
(II)

in which $R^1$, $R^2$, $R^3$, $R^4$, $R^5$, $R^6$, X and n are as defined above, are reacted, for example, with a carboxylic acid of the formula (IV-3)

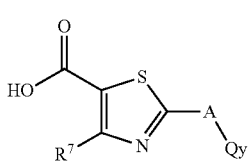
(IV-3)

in which $R^7$, A and Qy are as defined above
in the presence of a condensing agent.

Carboxylic acids of the formula (IV-3) are new. They can be prepared by the reaction scheme below, where $R^7$, A and Qy are as defined above and R is $C_1$-$C_6$-alkyl and Hal is halogen, from (XI). Compounds of the formula (XI) are known (e.g. J. Med. Chem. 49, 2006, 4721-4736). The reaction of (XI) to (XII) can be carried out by known methods (e.g. WO2005/113506). The further reaction via XIII to carboxylic acids of the formula (IV-3) can be carried out by known methods (e.g. WO2007/144100).

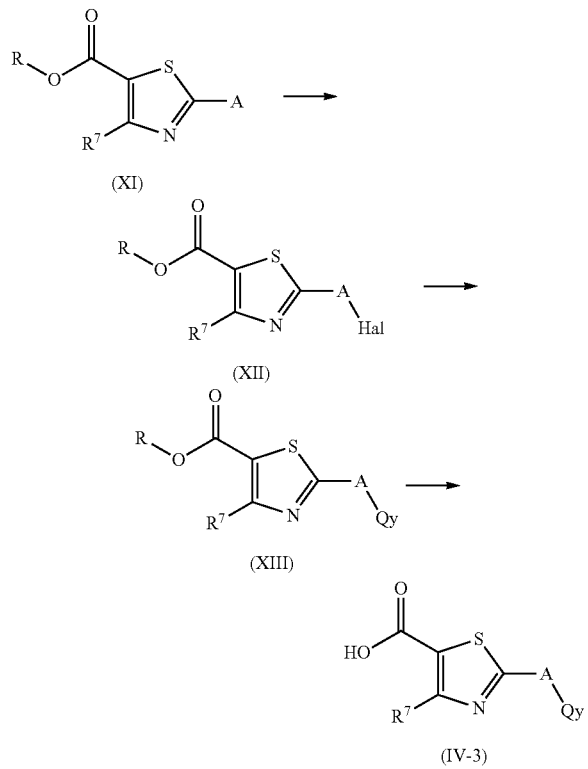

The active ingredients according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceuthorhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelle-*

*borni, Strongyloides stercoralis, Stronyloides* spp., *Taenia saginata, Taenia solium, Trichinella spiralis, Trichinella nativa, Trichinella britovi, Trichinella nelsoni, Trichinella pseudospiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Bus seola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix viridana, Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active ingredients with extenders, that is liquid solvents and/or solid carriers, optionally with the use of surfactants, that is emulsifiers and/or dispersants and/or foam-formers. The formulations are prepared either in suitable apparatuses or else before or during the application.

Suitable for use as auxiliaries are substances which are suitable for imparting to the composition itself and/or to preparations derived therefrom (for example spray liquors, seed dressings) particular properties, such as certain technical properties and/or else particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active ingredient, preferably between 0.5 and 90%.

The active ingredient of the invention may be present, in its commercial formulations and in the appropriate forms prepared from these formulations, in a mixture with other active ingredients such as insecticides, attractants, sterilants, bactericides, acaricides, nematicides, fungicides, growth regulators, herbicides, safeners, fertilizers and semiochemicals. In particular the active ingredients of the invention may be used in combination with further (auxiliary) agents for boosting activity.

When used as insecticides, the active ingredients according to the invention can furthermore be present, in their commercially available formulations and in the application forms prepared from these formulations, as a mixture with synergists. Synergists are compounds which increase the action of the active ingredients without it being necessary for the synergistic agent added to be active itself.

When used as insecticides, the active ingredients according to the invention can furthermore be present, in their commercially available formulations and in the application forms prepared from these formulations, as mixtures with inhibitors which reduce degradation of the active ingredient after use in the environment of the plant, on the surface of parts of plants or in plant tissues.

The active ingredient content of the application forms prepared from the commercially available formulations can vary within wide ranges. The active ingredient concentration of the application forms can be from 0.00000001 to 95% by weight of active ingredient, preferably between 0.00001 and 1% by weight.

The compounds are employed in a customary manner appropriate for the application forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active ingredients is carried out directly or by allowing the active ingredients to act on the surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape.

Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA (a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The active ingredients according to the invention are active not only against plant pests, hygiene pests and stored-product pests but also in the veterinary field against animal parasites (ecto and endoparasites) such as hard ticks, soft ticks, scab mites, harvest mites, flies (stinging and licking), parasitic fly larvae, lice, hair lice, bird lice and fleas. These parasites include:

from the order of the Anoplurida, for example *Haematopinus* spp., *Linognathus* spp., *Pediculus* spp., *Phtirus* spp., *Solenopotes* spp.

from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

from the order of the Siphonapterida, for example *Pulex* spp., *Ctenocephalides* spp., *Xenopsylla* spp., *Ceratophyllus* spp.

from the order of the Heteropterida, for example *Cimex* spp., *Triatoma* spp., *Rhodnius* spp., *Panstrongylus* spp.

from the order of the Blattarida, for example *Blatta orientalis, Periplaneta americana, Blattela germanica, Supella* spp.

from the subclass of the Acari (Acarina) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonys sus* spp., *Sternostoma* spp., *Varroa* spp.

from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active ingredients of the formula (I) according to the invention are also suitable for controlling arthropods, agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods it is intended to reduce deaths and improve performance (in the case of meat, milk, wool, hides, eggs, honey and the like) so that more economical and simpler animal keeping is made possible by the use of the active ingredients according to the invention.

In the veterinary field and in animal keeping, the active ingredients according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-ingredient-comprising shaped articles such as collars, ear tags, tail tags, limb bands, halters, marking devices and the like.

When used for livestock, poultry, domestic animals and the like, the active ingredients of the formula (I) can be applied as formulations (for example powders, emulsions, flowables) which comprise the active ingredients in an amount of from 1 to 80% by weight, either directly or after 100- to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*;

Hymenopterons, such as *Sirex juvencus, Urocerus gigas, Urocerus gigas taignus, Urocerus augur*;

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*;

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional mixing partners, reference is made to the abovementioned insecticides and fungicides.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces such as, for example, dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active ingredients, such as phosphoric esters, carbamates, pyrethroids, neonicotinoids, growth regulators or active ingredients from other known classes of insecticides.

They are used in aerosols, unpressurized spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, non-energized, or passive, evaporation systems, moth papers, moth bags and moth gels, as granules or dusts, in baits for scattering or in bait stations.

DESCRIPTION OF THE PREPARATION PROCESSES AND INTERMEDIATES

Anilines of the formula (II) are known (e.g. WO2007/043677, WO2008/126858, WO2008/126933) or can be prepared by known methods.

Carbonyl chlorides of the formula (III) in which Qx is pyrazole are known (e.g. WO2007/144100) or can be prepared by known methods.

Carboxylic acids of the formula (IV) in which Qx is pyrazole are known (e.g. WO2007/144100) or can be prepared by known methods.

Benzoxazinones of the formula (V) in which Qx is pyrazole are known (e.g. WO2007/144100) or can be prepared by known methods.

Hydrazines of the formula (VI) are known (e.g. WO2007/043677, WO2008/126858, WO2008/126933) or can be prepared by known methods.

Anthranilic hydrazides of the formula (VII) are new. They can be prepared in accordance with process C.

PREPARATION EXAMPLES

Synthesis of Carboxylic Acids of the Formula (IV-2)

Example A

IX

Synthesis of ethyl 2-(bromomethyl)-4-(2-chlorophenyl)pyrimidine-5-carboxylate

An amount of 820 mg (2.96 mmol) of ethyl 4-(2-chlorophenyl)-2-methylpyrimidine-5-carboxylate and 633 mg (3.55 mmol) of N-bromosuccinimide were dissolved in 18 ml of carbon tetrachloride and heated with stirring to boiling. At the heat of boiling, in portions, 49 mg (0.29 mmol) of 2,2'-azobis-2-methylpropanenitrile were added over 5 hours, followed by refluxing for a further hour. After cooling to room temperature, the reaction solution was filtered and the mother liquor was freed from the solvent under reduced pressure. The desired product was isolated by chromatographic purification.

(logP: 3.32; MH$^+$: 357; $^1$H-NMR (400 MHz, DMSO, δ, ppm): 1.00 (t, 3H), 4.12 (q, 2H), 4.80 (s, 2H), 7.50 (m, 4H), 9.30 (s, 1H).

Example B

X

Synthesis of ethyl 4-(2-chlorophenyl)-2-{[5-(trifluoromethyl)-2H-tetrazol-2-yl]methyl}-pyrimidine-5-carboxylate An amount of 345 mg (0.97 mmol) of ethyl 2-(bromomethyl)-4-(2-chlorophenyl)pyrimidine-5-carboxylate was added to a solution of 200 mg (1.45 mmol) of trifluoromethyltetrazole in 10 ml of acetonitrile. Then 174 mg (1.26 mmol) of potassium carbonate were added to the reaction solution, which was stirred at 60° C. for 6 hours. After cooling to room temperature, the reaction solution was filtered and the mother liquor was freed from the solvent under reduced pressure. The residue was admixed with 10 ml of water and extracted with ethyl acetate (3×20 ml). The combined organic phases were dried over sodium sulphate. The solvent was removed under reduced pressure and the residue was purified by chromatography.

(logP: 3.56; MH$^+$: 413; $^1$H-NMR (400 MHz, DMSO, δ, ppm): 0.99 (t, 3H), 4.13 (q, 2H) 6.62 (s, 2H), 7.50 (m, 4H), 9.28 (s, 1H).

Example C

IV-2

Synthesis of 4-(2-chlorophenyl)-2-{[5-(trifluoromethyl)-2H-tetrazol-2-yl]methyl}pyrimidine-5-carboxylic acid An amount of 1.74 g (4.21 mmol) of ethyl 4-(2-chlorophenyl)-2-{[5-(trifluoromethyl)-2H-tetrazol-2-yl]methyl}pyrimidine-5-carboxylate was dissolved in 12 ml of ethanol and the solution was admixed dropwise at 0° C. with 45% strength aqueous sodium hydroxide solution (5.05 mmol). The reaction was stirred for a further hour and warmed to RT. The ethanol was then removed under reduced pressure and the residue was admixed with ice-water (10 ml). The aqueous phase was extracted with ethyl acetate. The organic phase was discarded. Then the aqueous phase was adjusted to a pH of 3 using hydrochloric acid, and again extracted with ethyl acetate (3×20 ml). The combined organic phases were dried over sodium sulphate.

(logP: 2.50; MH$^+$: 385; $^1$H-NMR (400 MHz, DMSO, δ, ppm): 6.59 (s, 2H), 7.48 (m, 4H), 9.27 (s, 1H).

PREPARATION EXAMPLES

The preparation processes described above can be used to give the compounds of the formula (I)—for example the following compounds of the formula (I):

Example 1

Synthesis of methyl N'-(5-chloro-2-{[2-(3-chloropyridin-2-yl)-5-(5-heptalluoropropyltetrazol-2-ylmethyl)-2H-pyrazole-3-carbonyl]amino}-3-methylbenzoyl)-N-methylhydrazinecarboxylate An amount of 250 mg (0.40 mmol) of 6-chloro-2-[2-(3-chloropyridin-2-yl)-5-(5-heptafluoropropyltetrazol-2-ylmethyl)-2H-pyrazol-3-yl]-8-methyl-3,1-benzoxazin-4-one was dissolved in 20 ml of tetrahydrofuran and admixed with 209 mg (2.06 mmol) of methyl N-methylhydrazinecarboxylate. The mixture was first stirred at room temperature for 3 h and then heated under reflux for 16 h.

After cooling, the reaction mixture was freed from the solvent under reduced pressure. The desired product was isolated by chromatographic purification of the residue (logP: 3.66; MH$^+$: 727; $^1$H-NMR (400 MHz, DMSO, δ, ppm): 2.07 (s, 3H), 2.88 (s, 3H), 3.45 (br s, 3H), 6.35 (s, 2H), 7.29 (bs, 1H), 7.38 (s, 1H), 7.54 (d, 1H), 7.58 (dd, 1H), 8.13 (dd, 1H), 8.45 (dd, 1H), 10.24 (s, 1H), 10.46 (s, 1H)).

Example 2

Methyl N'-(2-{[2-(3-chloropyridin-2-yl)-5-(5-heptalluoropropyltetrazol-2-ylmethyl)-2H-pyrazole-3-carbonyl]amino}-5-iodo-3-methylbenzoyl)hydrazincarboxylate An amount of 583 mg (0.78 mmol) of N-(2-hydrazinocarbonyl-4-iodo-6-methylphenyl)-2-(3-chloropyridin-2-yl)-5-(5-heptafluoropropyltetrazol-2-ylmethyl)-2H-pyrazole-3-carboxamide was dissolved in 25 ml of pyridine and the solution was admixed dropwise with 84 mg (0.89 mmol) of methyl chloroformate. The mixture was stirred at room temperature for 2 h and freed from the solvent under reduced pressure. The desired product was isolated by chromatographic purification of the residue (logP: 3.58; MH$^+$: 805; $^1$H-NMR (400 MHz, DMSO, δ, ppm): 2.10 (s, 3H), 3.59 (br s, 3H), 6.34 (s, 2H), 7.34 (s, 1H), 7.58 (dd, 1H), 7.68 (br s, 1H), 7.81 (d, 1H), 8.14 (dd, 1H), 8.47 (dd, 1H), 9.24 (bs, 1H), 10.08 (s, 1H), 10.18 (s, 1H)).

The following examples can be obtained analogously:

The table gives, for Example 1, the complete NMR signals, and for the further examples a combination of logP, mass (MH$^+$) and those NMR signals which relate to the part of the molecule introduced last in the process.

| Ex. | Structure | logP | MH$^+$ | $^1$H-NMR (400 MHz, DMSO, δ, ppm), selected signals |
|---|---|---|---|---|
| 1 | [structure] | 3.66 | 727 | 2.07 (s, 3H), 2.88 (s, 3H), 3.45 (br s, 3H), 6.35 (s, 2H), 7.29 (bs, 1H), 7.38 (s, 1H), 7.54 (d, 1H), 7.58 (dd, 1H), 8.13 (dd, 1H), 8.45 (dd, 1H), 10.24 (s, 1H), 10.46 (s, 1H) |

-continued

| Ex. | Structure | logP | MH+ | ¹H-NMR (400 MHz, DMSO, δ, ppm), selected signals |
|---|---|---|---|---|
| 2 | 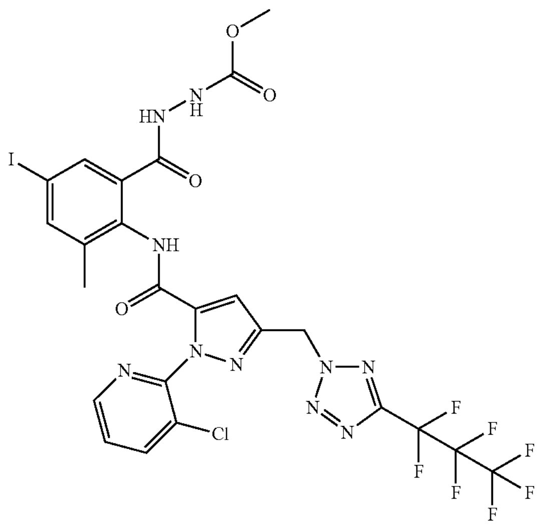 [SMILES: COC(=O)NNC(=O)c1cc(I)cc(C)c1NC(=O)c1cc(Cn2nnc(C(F)(F)C(F)(F)C(F)(F)F)n2)nn1-c1ncccc1Cl] | 3.58 | 805 | 2.10 (s, 3H), 3.59 (br s, 3H), 6.34 (s, 2H), 7.34 (s, 1H), 7.58 (dd, 1H), 7.68 (br s, 1H), 7.81 (d, 1H), 8.14 (dd, 1H), 8.47 (dd, 1H), 9.24 (bs, 1H), 10.08 (s, 1H), 10.18 (s, 1H) |
| 3 | 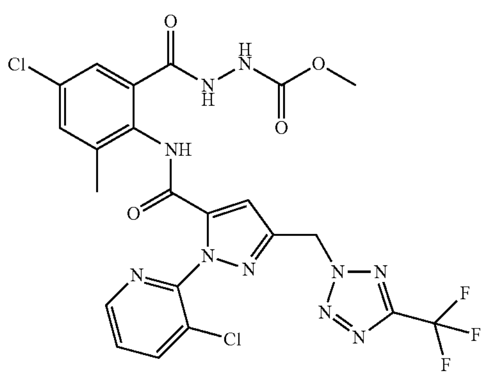 [SMILES: COC(=O)NNC(=O)c1cc(Cl)cc(C)c1NC(=O)c1cc(Cn2nnc(C(F)(F)F)n2)nn1-c1ncccc1Cl] | 2.73 (acidic) | 613 | 3.11 (br s, 3H, OMe), 8.95 (s, NH), 9.95 (s, NH), 10.02 (s, NH) |
| 4 | 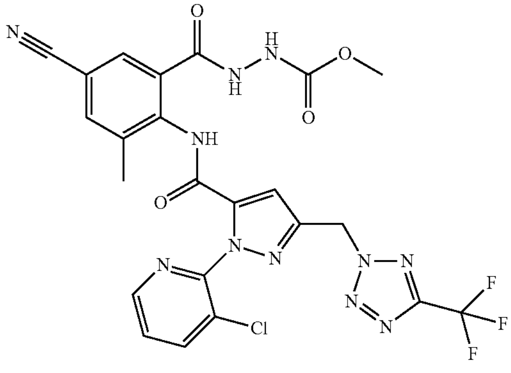 [SMILES: COC(=O)NNC(=O)c1cc(C#N)cc(C)c1NC(=O)c1cc(Cn2nnc(C(F)(F)F)n2)nn1-c1ncccc1Cl] | 2.41 (acidic) | 604 | 3.57 (br s, 3H, OMe), 8.99 (s, NH), 10.08 (s, NH), 10.29 (s, NH) |

-continued

| Ex. | Structure | logP | MH+ | ¹H-NMR (400 MHz, DMSO, δ, ppm), selected signals |
|---|---|---|---|---|
| 5 | 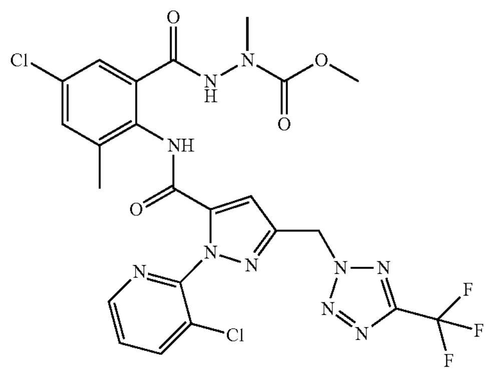 [SMILES: COC(=O)N(C)NC(=O)c1cc(Cl)cc(C)c1NC(=O)c1cc(Cn2nnc(C(F)(F)F)n2)nn1-c1ncccc1Cl] | 2.96 (acidic) | 627 | 2.93 (s, 3H, NMe), 3.52 (br s, 3H, OMe), 10.05 (s, NH). 10.29 (s, NH) |
| 6 | 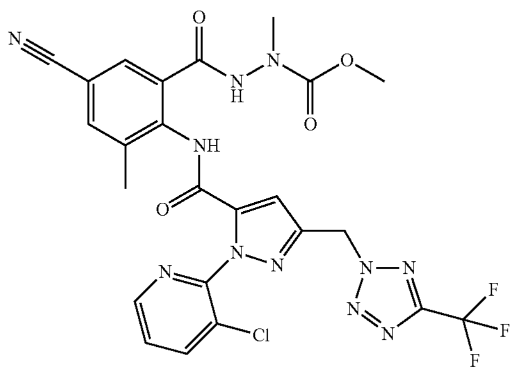 | 2.63 (acidic) | 618 | 2.93 (s, 3H, NMe), 3.59 (br s, 3H, OMe), 10.29 (s, NH), 10.40 (s, NH) |
| 7 | 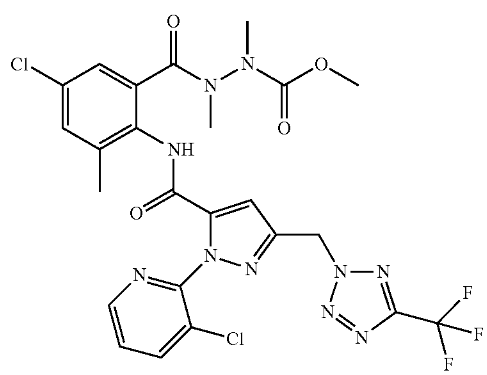 [SMILES: COC(=O)N(C)N(C)C(=O)c1cc(Cl)cc(C)c1NC(=O)c1cc(Cn2nnc(C(F)(F)F)n2)nn1-c1ncccc1Cl] | 3.39 (acidic) | 641 | 2.73; 2.82; 2.92 (s, 3H, NMe), 3.42; 3.62 (brs, 3H, OMe) |
| 8 | 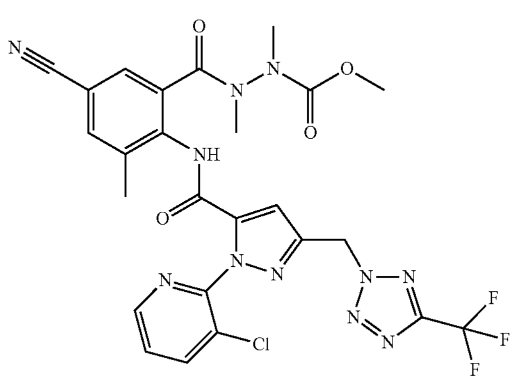 [SMILES: COC(=O)N(C)N(C)C(=O)c1cc(C#N)cc(C)c1NC(=O)c1cc(Cn2nnc(C(F)(F)F)n2)nn1-c1ncccc1Cl] | 2.97 (acidic) | 632 | 2.76; 2.82; 2.91 (s, 3H, NMe), 3.42; 3.61 (br s, 3H, OMe) |

-continued

| Ex. | Structure | logP | MH+ | ¹H-NMR (400 MHz, DMSO, δ, ppm), selected signals |
|---|---|---|---|---|
| 9 | 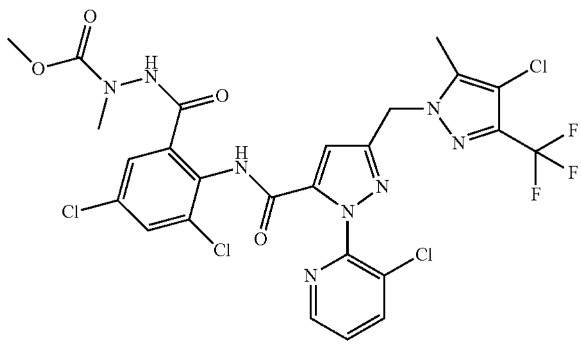 [SMILES: COC(=O)N(C)NC(=O)c1cc(Cl)cc(Cl)c1NC(=O)c1cc(Cn2nc(C(F)(F)F)c(Cl)c2C)nn1-c1ncccc1Cl] | 4.54 | 853 | 2.85 (s, 3H), 3.43; 3.60 (br s, 3H), 10.31 (s, NH), 10.43 (s, NH), |
| 10 | 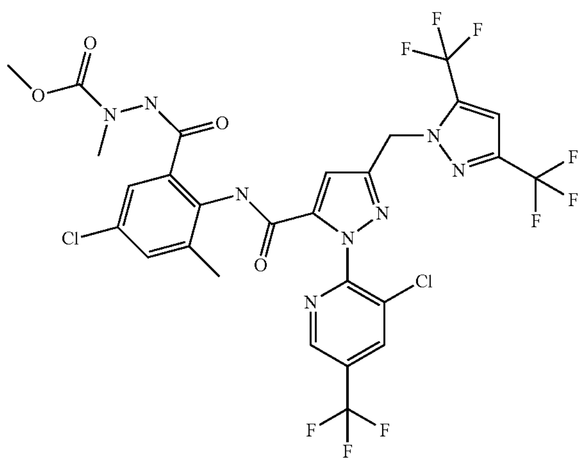 [SMILES: COC(=O)N(C)NC(=O)c1cc(Cl)cc(C)c1NC(=O)c1cc(Cn2nc(C(F)(F)F)cc2C(F)(F)F)nn1-c1ncc(C(F)(F)F)cc1Cl] | 4.35 | 761 | 2.86 (s, 3H), 3.44; 3.66 (br s, 3H), 10.35 (s, NH), 10.47 (s, NH) |
| 11 | 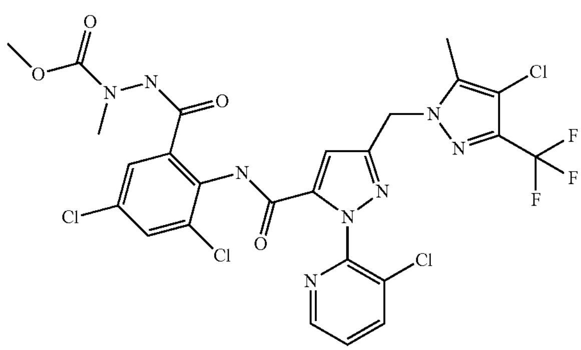 | 3.55 | 693 | 2.86 (s, 3H), 3.44; 3.71 (br s, 3H), 10.48 (s, NH), 10.58 (s, NH) |
| 12 | 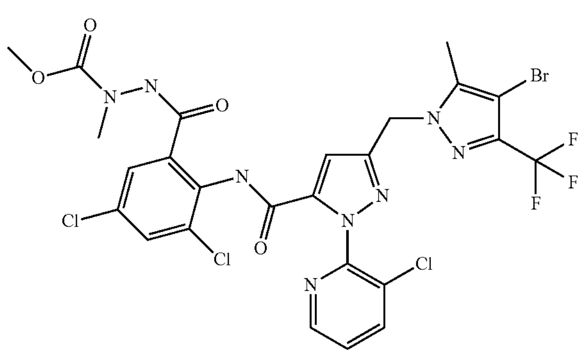 [SMILES: COC(=O)N(C)NC(=O)c1cc(Cl)cc(Cl)c1NC(=O)c1cc(Cn2nc(C(F)(F)F)c(Br)c2C)nn1-c1ncccc1Cl] | 3.57 | 737 | 2.87 (s, 3H), 3.45; 3.71 (br s, 3H), 10.49 (s, NH), 10.58 (s, NH) |

US 8,410,106 B2
43                                                                 44
-continued
| Ex. | Structure | logP | MH+ | 1H-NMR (400 MHz, DMSO, δ, ppm), selected signals |
|---|---|---|---|---|
| 13 | 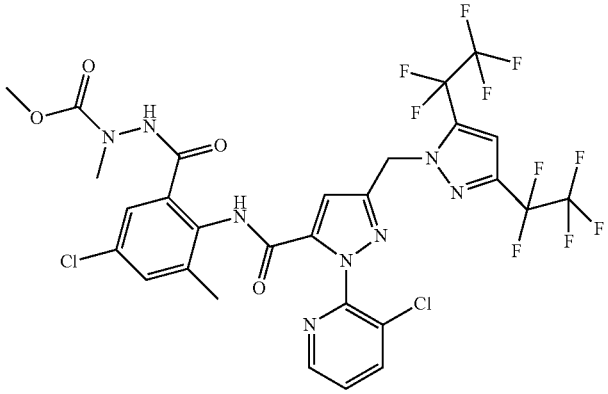 [SMILES: COC(=O)N(C)NC(=O)c1cc(Cl)cc(C)c1NC(=O)c1cc(Cn2nc(C(F)(F)C(F)(F)F)cc2C(F)(F)C(F)(F)F)nn1-c1ncccc1Cl] | 4.32 | 793 | 2.86 (s, 3H), 3.45; 3.71 (br s, 3H), 10.24 (s, NH), 10.46 (s, NH) |
| 14 | 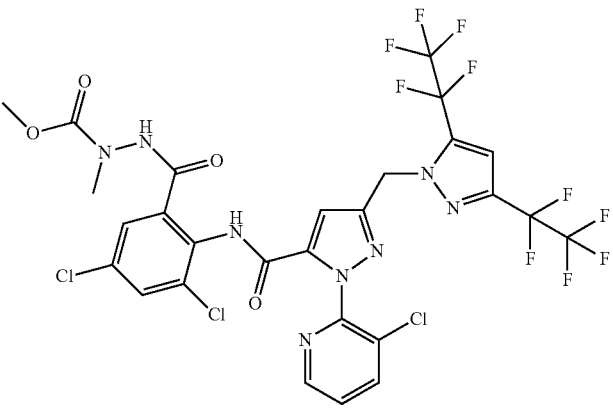 [SMILES: COC(=O)N(C)NC(=O)c1cc(Cl)cc(Cl)c1NC(=O)c1cc(Cn2nc(C(F)(F)C(F)(F)F)cc2C(F)(F)C(F)(F)F)nn1-c1ncccc1Cl] | 4.30 | 815 | 2.86 (s, 3H), 3.45; 3.62 (br s, 3H), 10.51 (s, NH), 10.58 (s, NH) |
| 15 | 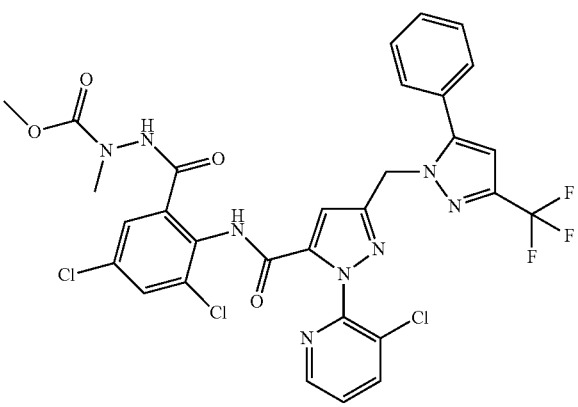 [SMILES: COC(=O)N(C)NC(=O)c1cc(Cl)cc(Cl)c1NC(=O)c1cc(Cn2nc(C(F)(F)F)cc2-c2ccccc2)nn1-c1ncccc1Cl] | 3.82 | 721 | 2.86 (s, 3H), 3.45; 3.62 (br s, 3H), 10.51 (s, NH), 10.58 (s, NH) |
| 16 | 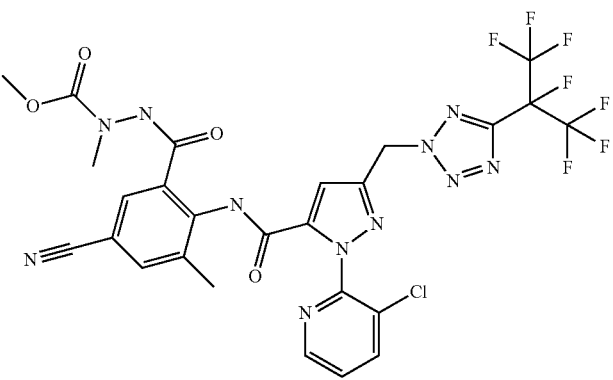 [SMILES: COC(=O)N(C)NC(=O)c1cc(C#N)cc(C)c1NC(=O)c1cc(Cn2nnc(C(F)(C(F)(F)F)C(F)(F)F)n2)nn1-c1ncccc1Cl] | 3.26 | 718 | 2.87 (s, 3H), 3.46; 3.65 (br s, 3H), 10.49 (s, NH), 10.55 (s, NH) |

-continued

| Ex. | Structure | logP | MH+ | ¹H-NMR (400 MHz, DMSO, δ, ppm), selected signals |
|---|---|---|---|---|
| 17 | 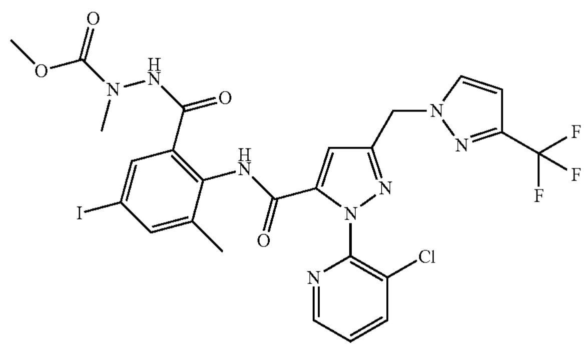 [SMILES: COC(=O)N(C)NC(=O)c1cc(I)cc(C)c1NC(=O)c1cc(Cn2ccc(C(F)(F)F)n2)nn1-c1ncccc1Cl] | 3.01 | 717 | 2.87 (s, 3H), 3.44; 3.64 (br s, 3H), 10.16 (s, NH), 10.39 (s, NH) |
| 18 | 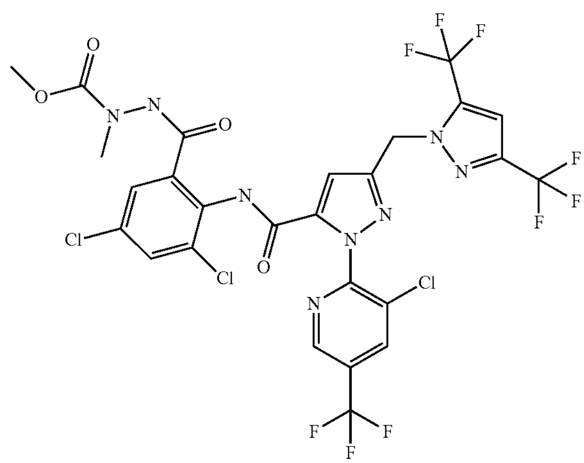 | 4.32 | 781 | CD$_3$CN: 2.99 (s, 3H), 3.46; 3.66 (br s, 3H), 9.02 (s, NH) |
| 19 | 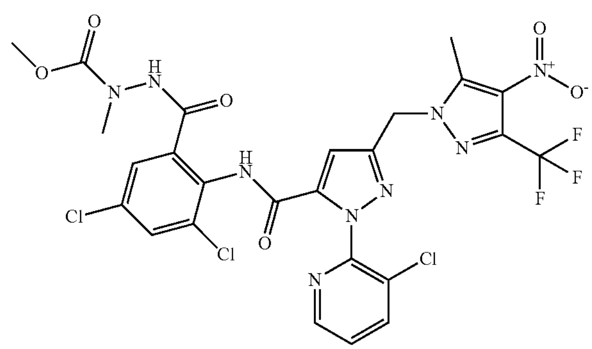 [SMILES: COC(=O)N(C)NC(=O)c1cc(Cl)cc(Cl)c1NC(=O)c1cc(Cn2nc(C(F)(F)F)c([N+](=O)[O-])c2C)nn1-c1ncccc1Cl] | 3.11 | 706 | 2.86 (s, 3H), 3.47; 3.62 (br s, 3H), 10.47 (s, NH), 10.57 (s, NH) |
| 20 | 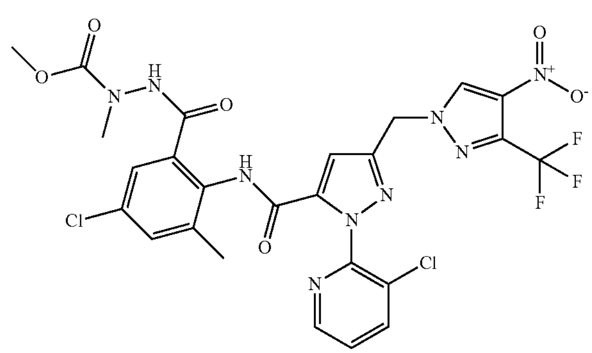 [SMILES: COC(=O)N(C)NC(=O)c1cc(Cl)cc(C)c1NC(=O)c1cc(Cn2cc([N+](=O)[O-])c(C(F)(F)F)n2)nn1-c1ncccc1Cl] | 3.07 | 670 | CD$_3$CN: 3.04 (s, 3H), 3.48; 3.66 (br s, 3H), 8.76 (s, NH), 9.06 (s, NH) |

-continued

| Ex. | Structure | logP | MH+ | ¹H-NMR (400 MHz, DMSO, δ, ppm), selected signals |
|---|---|---|---|---|
| 21 | 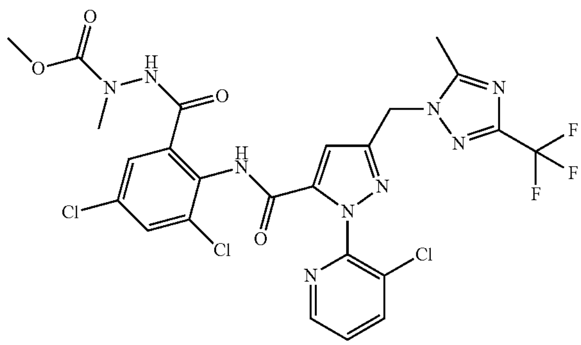 [SMILES: COC(=O)N(C)NC(=O)c1cc(Cl)cc(Cl)c1NC(=O)c1cc(Cn2nc(C(F)(F)F)nc2C)nn1-c1ncccc1Cl] | 2.51 | 662 | 2.87 (s, 3H), 3.45; 3.64 (br s, 3H), 10.47 (s, NH), 10.56 (s, NH) |
| 22 | 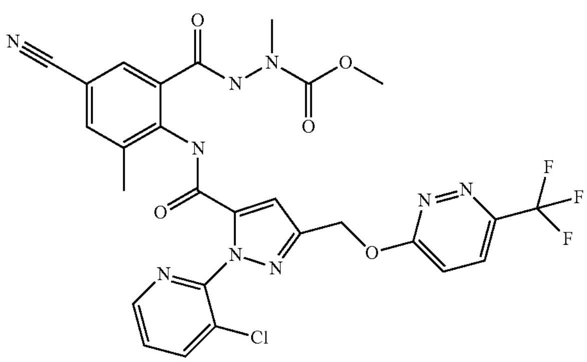 [SMILES: COC(=O)N(C)NC(=O)c1cc(C#N)cc(C)c1NC(=O)c1cc(COc2ccc(C(F)(F)F)nn2)nn1-c1ncccc1Cl] | 2.53 (acidic) | 644 | 2.88 (s, 3H, NMe), 3.50 (br s, 3H, OMe), 10.45 (s, NH), 10.55 (s, NH) |
| 23 | 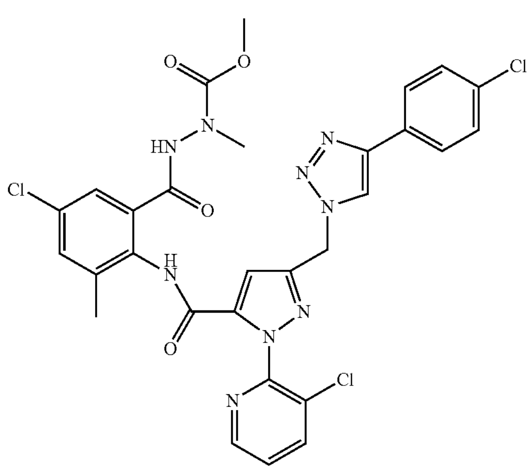 [SMILES: COC(=O)N(C)NC(=O)c1cc(Cl)cc(C)c1NC(=O)c1cc(Cn2cc(-c3ccc(Cl)cc3)nn2)nn1-c1ncccc1Cl] | 3.14 | 668 | 2.87 (s, 3H), 3.58 (s, 3H) |

-continued

| Ex. | Structure | logP | MH+ | ¹H-NMR (400 MHz, DMSO, δ, ppm), selected signals |
|---|---|---|---|---|
| 24 | 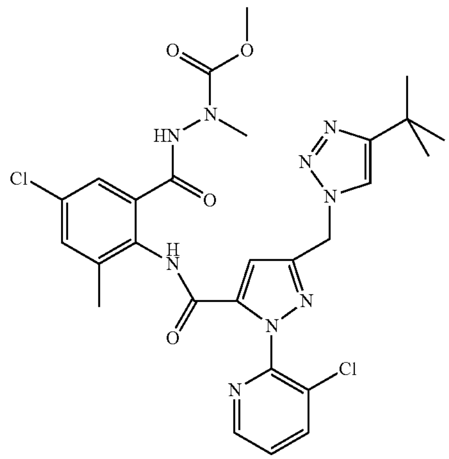 [SMILES: COC(=O)N(C)NC(=O)c1cc(Cl)cc(C)c1NC(=O)c1cc(Cn2cc(C(C)(C)C)nn2)nn1-c1ncccc1Cl] | 2.53 | 614 | 2.87 (s, 3H), 3.58 (s, 3H) |
| 25 | 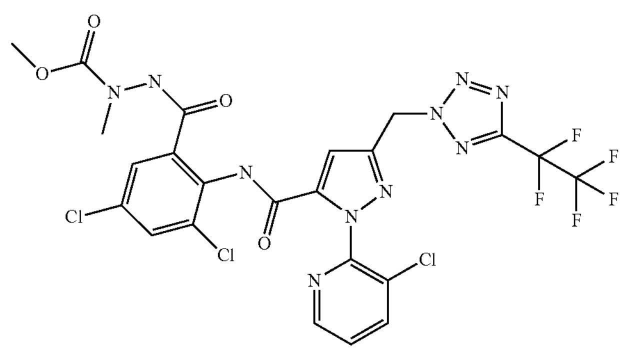 [SMILES: COC(=O)N(C)NC(=O)c1cc(Cl)cc(Cl)c1NC(=O)c1cc(Cn2nnc(C(F)(F)C(F)(F)F)n2)nn1-c1ncccc1Cl] | 3.32 | 697 | 2.87 (s, 3H), 3.45; 3.63 (br s, 3H), 10.54 (s, NH), 10.57 (s, NH) |
| 26 | 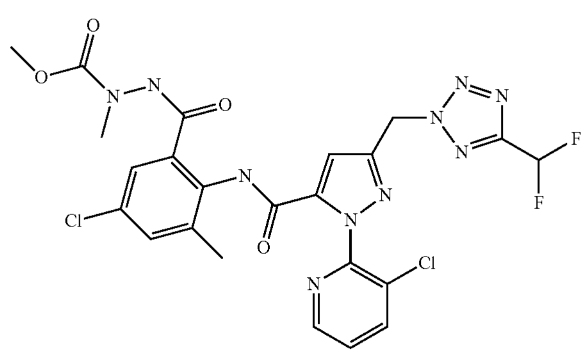 | 2.49 | 609 | 2.88 (s, 3H), 3.47; 3.63 (br s, 3H), 10.22 (s, NH), 10.45 (s, NH) |
| 27 | 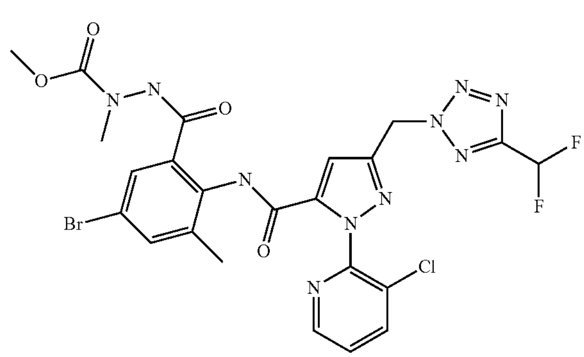 [SMILES: COC(=O)N(C)NC(=O)c1cc(Cl)cc(C)c1NC(=O)c1cc(Cn2nnc(C(F)F)n2)nn1-c1ncccc1Cl] | 2.58 | 653 | 2.88 (s, 3H), 3.48; 3.62 (br s, 3H), 10.21 (s, NH), 10.45 (s, NH) |

-continued

| Ex. | Structure | logP | MH+ | ¹H-NMR (400 MHz, DMSO, δ, ppm), selected signals |
|---|---|---|---|---|
| 28 | 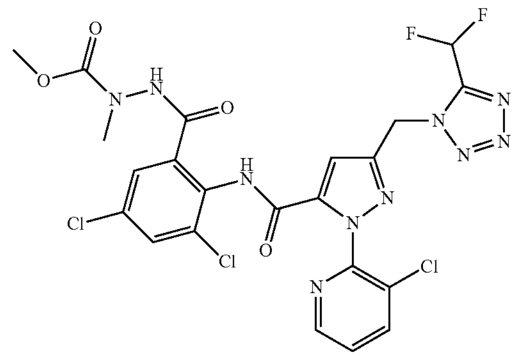 [SMILES: COC(=O)N(C)NC(=O)c1cc(Cl)cc(Cl)c1NC(=O)c1cc(Cn2nnnc2C(F)F)nn1-c1ncccc1Cl] | 2.27 | 629 | 2.87 (s, 3H), 3.47; 3.64 (br s, 3H), 10.52 (s, NH), 10.57 (s, NH) |
| 29 | 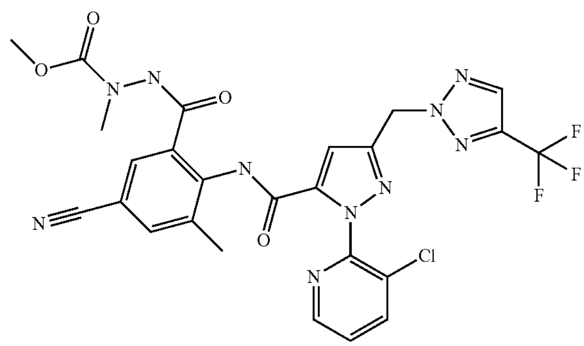 [SMILES: COC(=O)N(C)NC(=O)c1cc(C#N)cc(C)c1NC(=O)c1cc(Cn2ncc(C(F)(F)F)n2)nn1-c1ncccc1Cl] | 2.62 | 617 | 2.87 (s, 3H), 3.46; 3.65 (br s, 3H), 10.43 (s, NH), 10.54 (s, NH) |
| 30 | 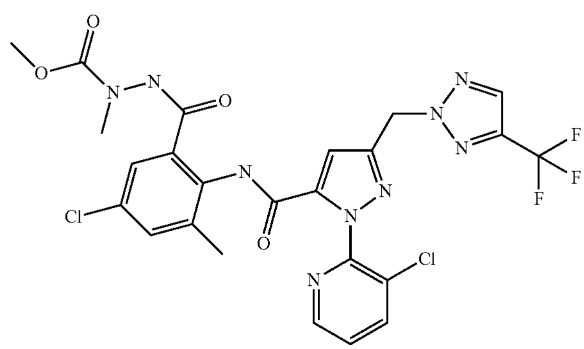 | 2.94 | 626 | 2.88 (s, 3H), 3.44; 3.65 (br s, 3H), 10.19 (s, NH), 10.44 (s, NH) |
| 31 | 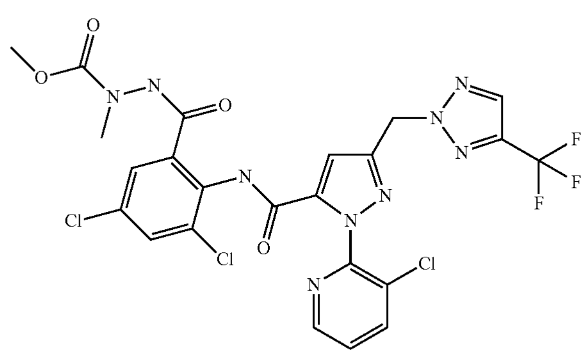 [SMILES: COC(=O)N(C)NC(=O)c1cc(Cl)cc(C)c1NC(=O)c1cc(Cn2ncc(C(F)(F)F)n2)nn1-c1ncccc1Cl] | 2.94 | 648 | 2.87 (s, 3H), 3.44; 3.64 (br s, 3H), 10.50 (s, NH), 10.56 (s, NH) |

-continued
| Ex. | Structure | logP | MH+ | ¹H-NMR (400 MHz, DMSO, δ, ppm), selected signals |
|---|---|---|---|---|
| 32 | 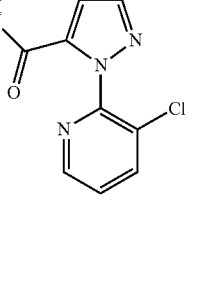 | 2.81 | 718 | 2.87 (s, 3H), 3.45; 3.65 (br s, 3H), 10.16 (s, NH), 10.42 (s, NH) |
| 33 | 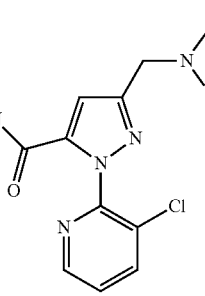 | 2.61 | 626 | CD₃CN: 3.04 (s, 3H), 3.47; 3.65 (br s, 3H), 8.74 (s, NH), 9.03 (s, NH) |
| 34 | 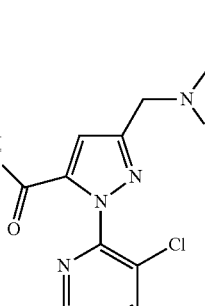 | 2.61 | 646 | CD₃CN: 2.97 (s, 3H), 3.49; 3.65 (br s, 3H), 8.82 (s, NH), 9.03 (s, NH) |
| 35 | 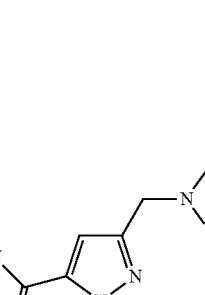 | 3.14 | 718 | 2.87 (s, 3H), 3.44; 3.64 (br s, 3H), 10.16 (s, NH), 10.40 (s, NH) |

-continued
| Ex. | Structure | logP | MH+ | ¹H-NMR (400 MHz, DMSO, δ, ppm), selected signals |
|---|---|---|---|---|
| 36 | 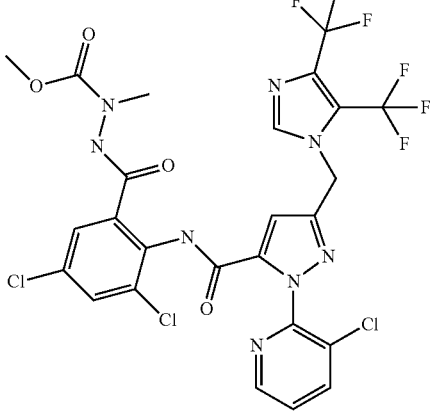 | 3.10 | 713 | 2.86 (s, 3H), 3.47; 3.64 (br s, 3H), 10.47 (s, NH), 10.40 (s, NH) |
| 37 | 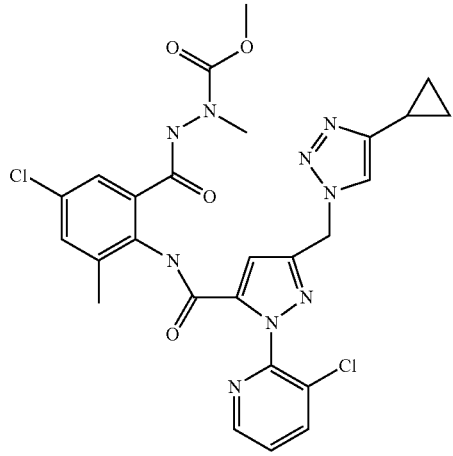 [SMILES: COC(=O)N(C)NC(=O)c1cc(Cl)cc(C)c1NC(=O)c1cc(Cn2cc(C3CC3)nn2)nn1-c1ncccc1Cl] | 2.18 | 598 | 2.88 (s, 3H), 3.61 (s, 3H) |
| 38 | 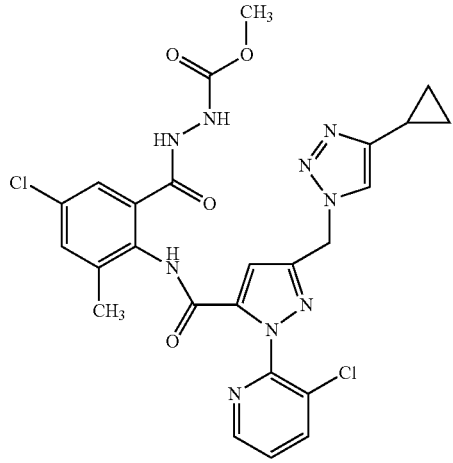 [SMILES: COC(=O)NNC(=O)c1cc(Cl)cc(C)c1NC(=O)c1cc(Cn2cc(C3CC3)nn2)nn1-c1ncccc1Cl] | 2.02 | 584 | 3.61 (s, 3H) |

-continued

| Ex. | Structure | logP | MH+ | ¹H-NMR (400 MHz, DMSO, δ, ppm), selected signals |
|---|---|---|---|---|
| 39 | 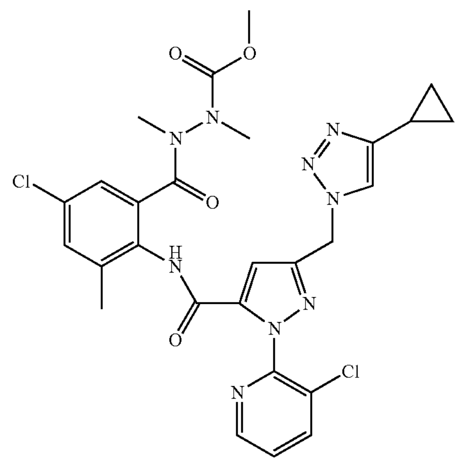 [SMILES: COC(=O)N(C)N(C)C(=O)c1cc(Cl)cc(C)c1NC(=O)c1cc(Cn2cc(C3CC3)nn2)nn1-c1ncccc1Cl] | 2.71 | 612 | 3.60 (s, 3H) |
| 40 | 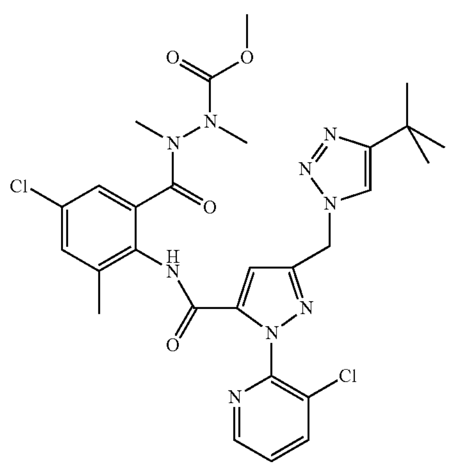 [SMILES: COC(=O)N(C)N(C)C(=O)c1cc(Cl)cc(C)c1NC(=O)c1cc(Cn2cc(C(C)(C)C)nn2)nn1-c1ncccc1Cl] | 2.98 | 628 | 3.59 (s, 3H) |
| 41 | 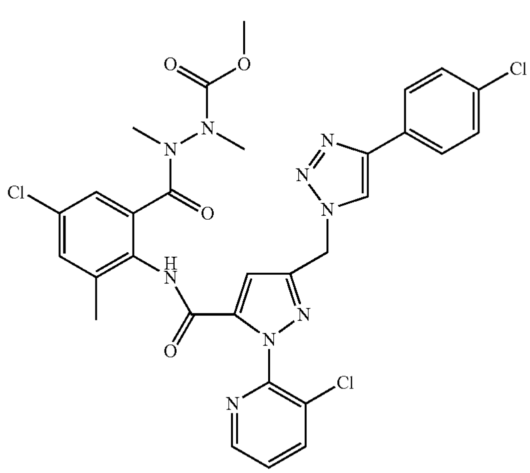 [SMILES: COC(=O)N(C)N(C)C(=O)c1cc(Cl)cc(C)c1NC(=O)c1cc(Cn2cc(-c3ccc(Cl)cc3)nn2)nn1-c1ncccc1Cl] | 3.49 | 682 | 3.60 (s, 3H) |

-continued

| Ex. | Structure | logP | MH+ | ¹H-NMR (400 MHz, DMSO, δ, ppm), selected signals |
|---|---|---|---|---|
| 42 | 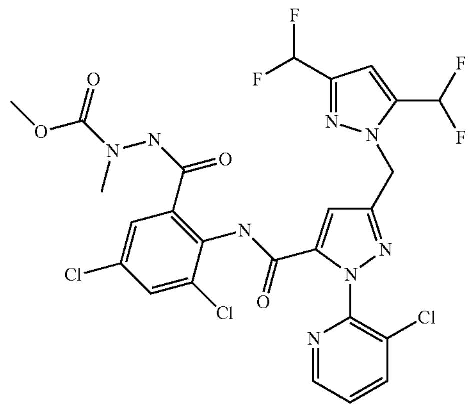 [SMILES: COC(=O)N(C)NC(=O)c1cc(Cl)cc(Cl)c1NC(=O)c1cc(Cn2nc(C(F)F)cc2C(F)F)nn1-c1ncccc1Cl] | 2.90 | 677 | 2.86 (s, 3H), 3.43; 3.62 (br s, 3H), 10.49 (s, NH), 10.54 (s, NH) |
| 43 | 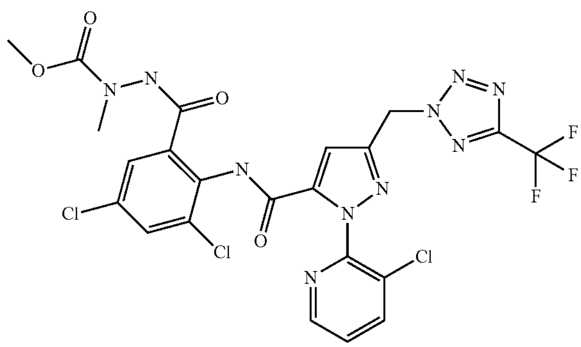 [SMILES: COC(=O)N(C)NC(=O)c1cc(Cl)cc(Cl)c1NC(=O)c1cc(Cn2nnc(C(F)(F)F)n2)nn1-c1ncccc1Cl] | 2.92 | 647 | 2.87 (s, 3H), 3.46; 3.64 (br s, 3H), 10.53 (s, NH), 10.57 (s, NH) |
| 44 | 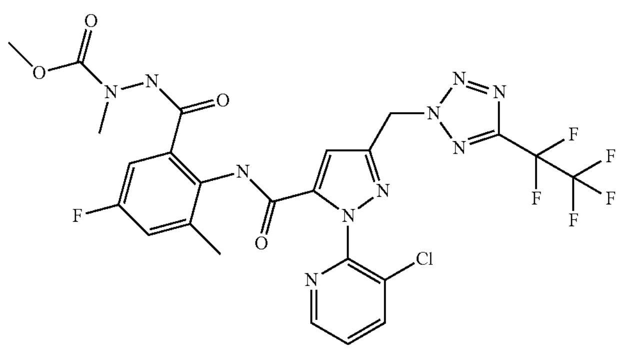 | 3.05 | 661 | 2.91 (s, 3H), 3.44; 3.65 (br s, 3H), 10.17 (s, NH), 10.43 (s, NH) |
| 45 | 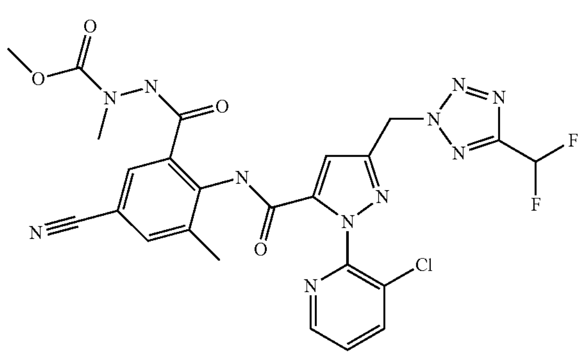 [SMILES: COC(=O)N(C)NC(=O)c1cc(C#N)cc(C)c1NC(=O)c1cc(Cn2nnc(C(F)F)n2)nn1-c1ncccc1Cl] | 2.15 | 600 | 2.87 (s, 3H), 3.47; 3.64 (br s, 3H), 10.46 (s, NH), 10.55 (s, NH) |

-continued

| Ex. | Structure | logP | MH+ | ¹H-NMR (400 MHz, DMSO, δ, ppm), selected signals |
|---|---|---|---|---|
| 46 | 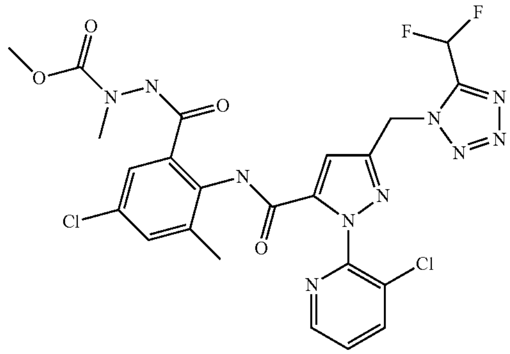 [SMILES: COC(=O)N(C)NC(=O)c1cc(Cl)cc(C)c1NC(=O)c1cc(Cn2nnnc2C(F)F)nn1-c1ncccc1Cl] | 2.25 | 609 | 2.88 (s, 3H), 3.40; 3.64 (br s, 3H), 10.21 (s, NH), 10.45 (s, NH) |
| 47 | 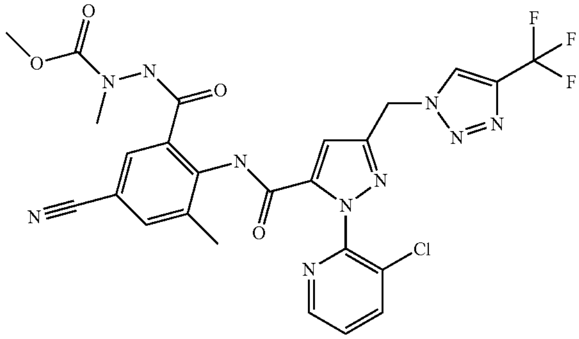 [SMILES: COC(=O)N(C)NC(=O)c1cc(C#N)cc(C)c1NC(=O)c1cc(Cn2cc(C(F)(F)F)nn2)nn1-c1ncccc1Cl] | 2.30 | 617 | CD₃CN: 3.03 (s, 3H), 3.50; 3.65 (br s, 3H), 8.88 (s, NH), 9.35 (s, NH) |
| 48 | 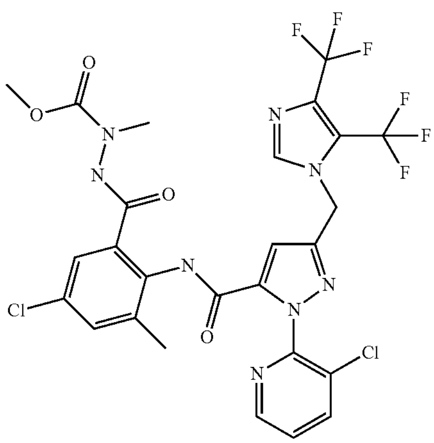 [SMILES: COC(=O)N(C)NC(=O)c1cc(Cl)cc(C)c1NC(=O)c1cc(Cn2cnc(C(F)(F)F)c2C(F)(F)F)nn1-c1ncccc1Cl] | 3.08 | 693 | 2.86 (s, 3H), 3.47; 3.65 (br s, 3H), 10.18 (s, NH), 10.45 (s, NH) |
| 49 | 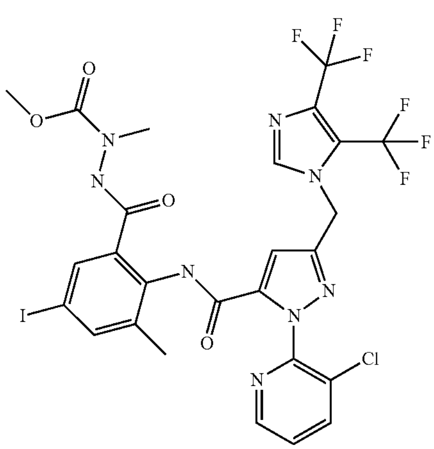 [SMILES: COC(=O)N(C)NC(=O)c1cc(I)cc(C)c1NC(=O)c1cc(Cn2cnc(C(F)(F)F)c2C(F)(F)F)nn1-c1ncccc1Cl] | 3.26 | 785 | 2.86 (s, 3H), 3.47; 3.65 (br s, 3H), 10.15 (s, NH), 10.42 (s, NH) |

-continued
| Ex. | Structure | logP | MH⁺ | $^1$H-NMR (400 MHz, DMSO, δ, ppm), selected signals |
|---|---|---|---|---|
| 50 | 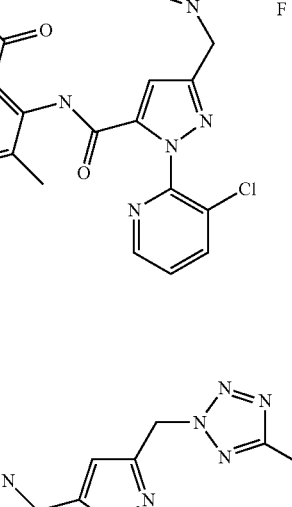 | 2.91 | 659 | 2.88 (s, 3H), 3.44; 3.64 (br s, 3H), 10.19 (s, NH), 10.43 (s, NH) |
| 51 | 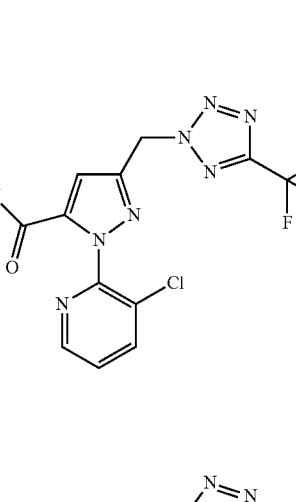 | 3.15 | 719 | 2.87 (s, 3H), 3.45; 3.64 (br s, 3H), 10.20 (s, NH), 10.43 (s, NH) |
| 52 | 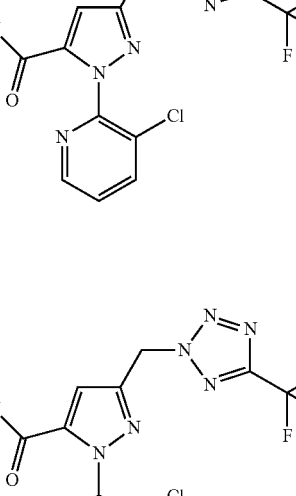 | 3.32 | 677 | 2.88 (s, 3H), 3.45; 3.65 (br s, 3H), 10.24 (s, NH), 10.46 (s, NH) |
| 53 | 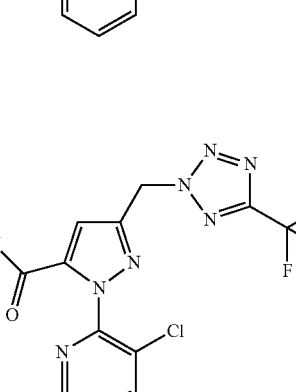 | 3.40 | 721 | 2.88 (s, 3H), 3.45; 3.64 (br s, 3H), 10.23 (s, NH), 10.46 (s, NH) |

-continued

| Ex. | Structure | logP | MH+ | ¹H-NMR (400 MHz, DMSO, δ, ppm), selected signals |
|---|---|---|---|---|
| 54 | 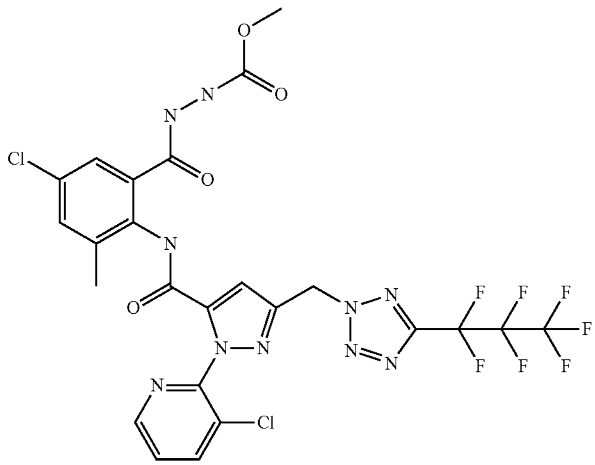 [SMILES: COC(=O)NNC(=O)c1cc(Cl)cc(C)c1NC(=O)c1cc(Cn2nnc(C(F)(F)C(F)(F)C(F)(F)F)n2)nn1-c1ncccc1Cl] | 3.41 | 713 | 3.61 (bs, 3H) |
| 55 | 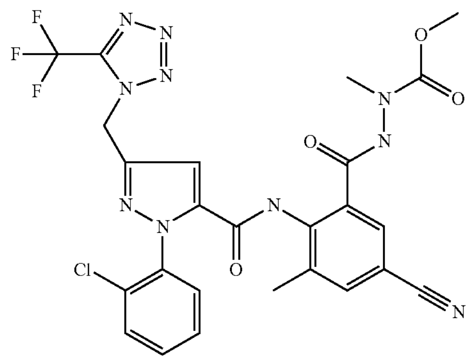 [SMILES: COC(=O)N(C)NC(=O)c1cc(C#N)cc(C)c1NC(=O)c1cc(Cn2nnnc2C(F)(F)F)nn1-c1ccccc1Cl] | 2.69 | 617 | 3.49 (br, 3H OCH3); 2.76 (s, 3H CH3); 7.95 (s, NH); 7.77 (s, NH) |
| 56 | 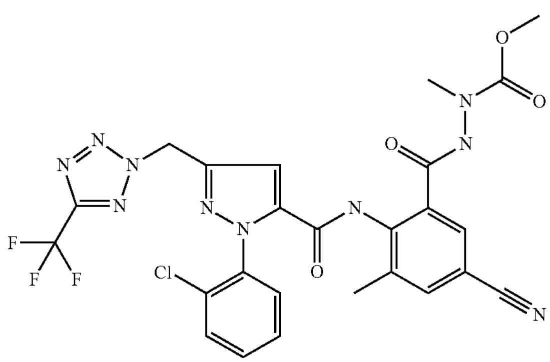 [SMILES: COC(=O)N(C)NC(=O)c1cc(C#N)cc(C)c1NC(=O)c1cc(Cn2nnc(C(F)(F)F)n2)nn1-c1ccccc1Cl] | 2.97 | 617 | 3.57 (br, 3H OCH3); 2.84 (s, 3H CH3); 7.67-7.77 (d, NH); 7.79-7.95 (d, NH) |
| 57 | 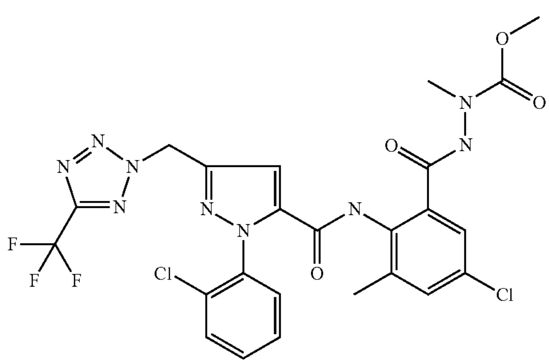 [SMILES: COC(=O)N(C)NC(=O)c1cc(Cl)cc(C)c1NC(=O)c1cc(Cn2nnc(C(F)(F)F)n2)nn1-c1ccccc1Cl] | 3.34 | 627 | 3.34 (br, 3H OCH3); 2.9 (s, 3H CH3); 7.49-7.5 (d, NH); 7.54-7.57 (d, NH) |

-continued

| Ex. | Structure | logP | MH+ | ¹H-NMR (400 MHz, DMSO, δ, ppm), selected signals |
|---|---|---|---|---|
| 58 | 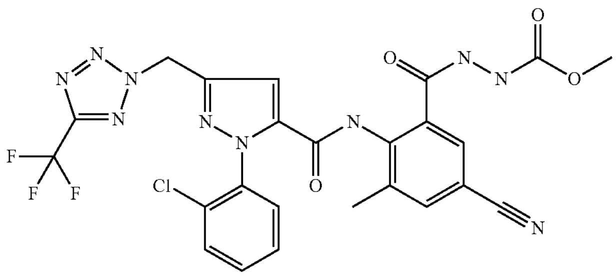 [SMILES: COC(=O)NNC(=O)c1cc(C#N)cc(C)c1NC(=O)c1cc(Cn2nnc(C(F)(F)F)n2)nn1-c1ccccc1Cl] | 2.79 | 604 | 3.52 (br, 3H OCH3); 7.54-7.56 (d, NH); 7.75 (s, NH); 7.94 (s, NH) |
| 59 | 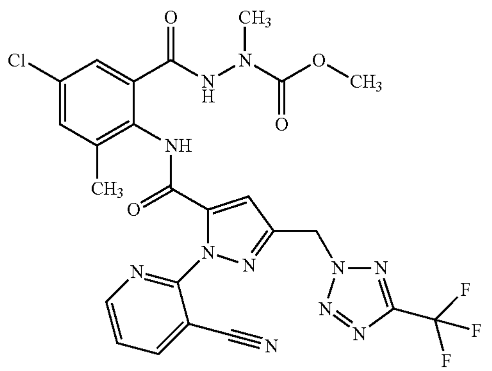 [SMILES: COC(=O)N(C)NC(=O)c1cc(Cl)cc(C)c1NC(=O)c1cc(Cn2nnc(C(F)(F)F)n2)nn1-c1ncccc1C#N] | 2.73 | 618 | 10.57 (s, NH), 10.42 (s, NH), 3.64 and 3.46 (br s, 3H), 2.90 (s, 3H) |
| 60 | 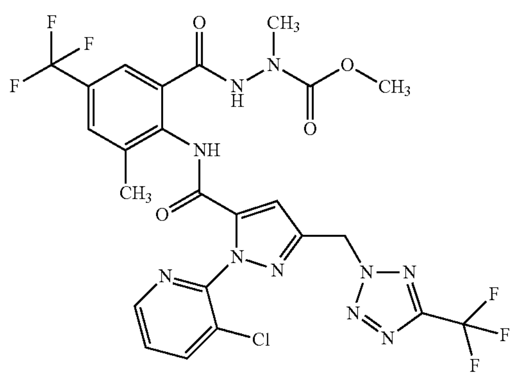 [SMILES: COC(=O)N(C)NC(=O)c1cc(C(F)(F)F)cc(C)c1NC(=O)c1cc(Cn2nnc(C(F)(F)F)n2)nn1-c1ncccc1Cl] | 3.17 | 661 | |
| 61 | 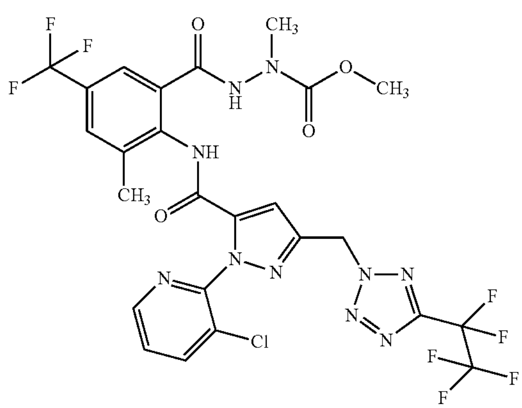 [SMILES: COC(=O)N(C)NC(=O)c1cc(C(F)(F)F)cc(C)c1NC(=O)c1cc(Cn2nnc(C(F)(F)C(F)(F)F)n2)nn1-c1ncccc1Cl] | 3.55 | 711 | 10.57 (s, NH), 10.44 (s, NH), 3.64 and 3.46 (br s, 3H), 2.90 (s, 3H) |

-continued

| Ex. | Structure | logP | MH+ | ¹H-NMR (400 MHz, DMSO, δ, ppm), selected signals |
|---|---|---|---|---|
| 62 | 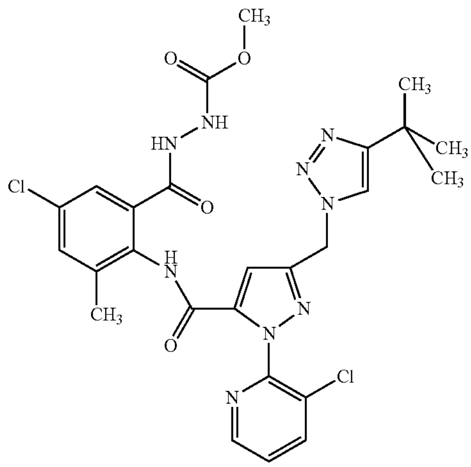 [SMILES: COC(=O)NNC(=O)c1cc(Cl)cc(C)c1NC(=O)c1cc(Cn2cc(C(C)(C)C)nn2)nn1-c1ncccc1Cl] | 2.38 (acidic) | 602 | 1.3 (s, 9H, tBu), 3.6 (br, s, 3H, OMe), 9.3 (br, s, 1H, NH), 11.1 (s, br, 1H, NH) |
| 63 | 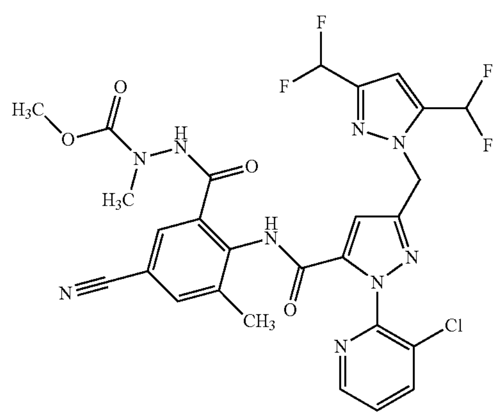 [SMILES: COC(=O)N(C)NC(=O)c1cc(C#N)cc(C)c1NC(=O)c1cc(Cn2nc(C(F)F)cc2C(F)F)nn1-c1ncccc1Cl] | 2.59 | 648 | 10.52 (s, NH)<br>10.42 (s, NH)<br>3.64 and 3.46 (br, s, 3H)<br>2.87 (s, 3H) |
| 64 | 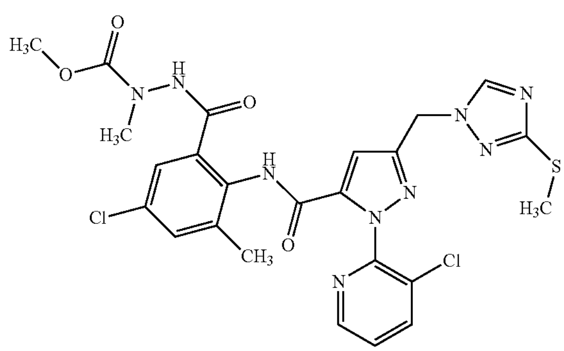 [SMILES: COC(=O)N(C)NC(=O)c1cc(Cl)cc(C)c1NC(=O)c1cc(Cn2cnc(SC)n2)nn1-c1ncccc1Cl] | 2.09 | 604/606 | NMR in CH₃CN:<br>9.07 (br, NH), 8.83 (s, NH), 3.70 and 3.46 (br, 3H), 3.03 (s, 3H) |
| 65 | 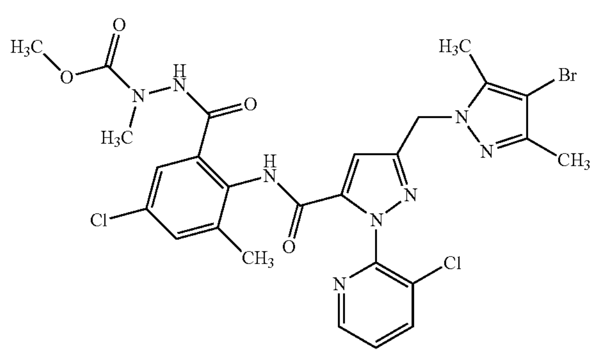 | 2.97 | 665 | 10.43 (s, NH)<br>10.12 (s, NH)<br>3.65 and 3.45 (br, s, 3H)<br>2.88 (s, 3H) |

-continued
| Ex. | Structure | logP | MH+ | ¹H-NMR (400 MHz, DMSO, δ, ppm), selected signals |
|---|---|---|---|---|
| 66 | 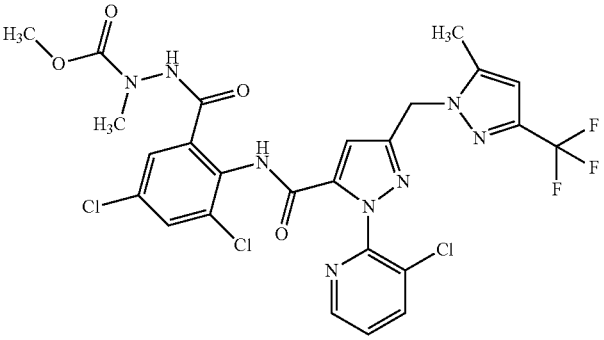 [SMILES: COC(=O)N(C)NC(=O)c1cc(Cl)cc(Cl)c1NC(=O)c1cc(Cn2nc(C(F)(F)F)cc2C)nn1-c1ncccc1Cl] | 3.10 | 659 | 10.54 (s, NH)<br>10.46 (s, NH)<br>3.63 and 3.44 (br, s, 3H)<br>2.86 (s, 3H) |
| 67 | 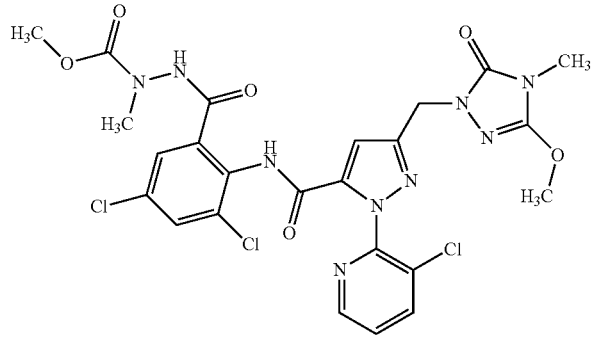 | 1.90 | 638 | 10.56 (s, NH)<br>10.43 (s, NH)<br>3.62 and 3.47 (br, s, 3H)<br>2.87 (s, 3H) |
| 68 | 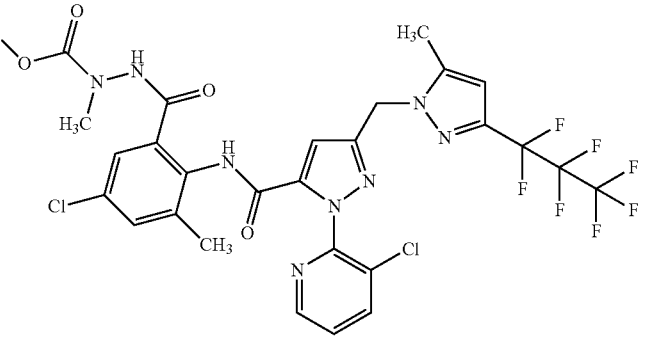 | 3.82 | 739 | NMR in CH₃CN:<br>8.90 (br, NH), 8.70 (s, NH), 3.70 and 3.45 (br, 3H), 3.03 (s, 3H) |
| 69 | 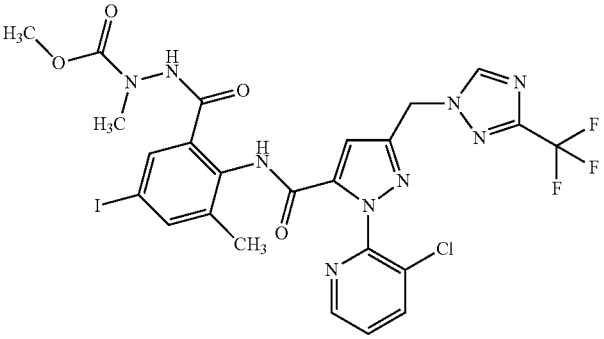 [SMILES: COC(=O)N(C)NC(=O)c1cc(I)cc(C)c1NC(=O)c1cc(Cn2cnc(C(F)(F)F)n2)nn1-c1ncccc1Cl] | 2.71 | 718 | NMR in CH₃CN:<br>9.04 (br, NH), 8.73 (s, NH), 3.69 and 3.50 (br, 3H), 3.04 (s, 3H) |

-continued

| Ex. | Structure | logP | MH+ | ¹H-NMR (400 MHz, DMSO, δ, ppm), selected signals |
|---|---|---|---|---|
| 70 | 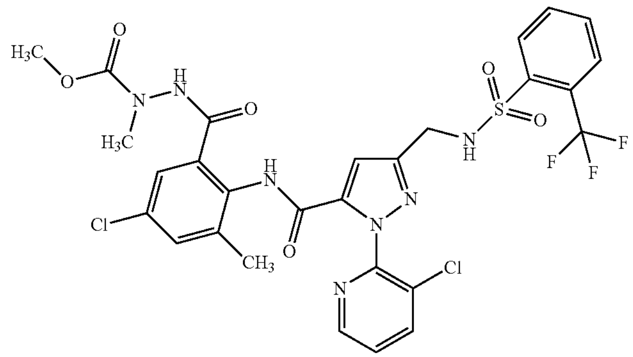 [SMILES: COC(=O)N(C)NC(=O)c1cc(Cl)cc(C)c1NC(=O)c1cc(CNS(=O)(=O)c2ccccc2C(F)(F)F)nn1-c1ncccc1Cl] | 2.81 | 714 | NMR in CH₃CN:<br>9.01 (br, NH), 8.78 (s, NH), 3.65 and 3.52 (br, 3H), 3.06 (s, 3H) |
| 71 | 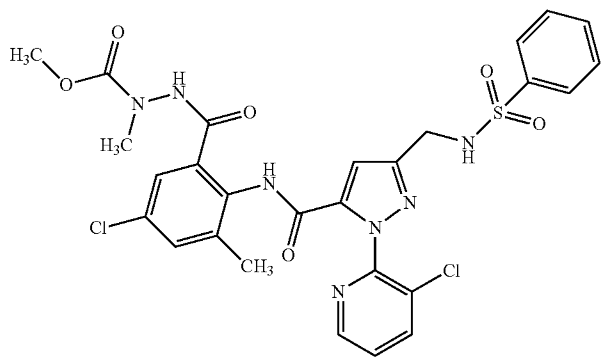 [SMILES: COC(=O)N(C)NC(=O)c1cc(Cl)cc(C)c1NC(=O)c1cc(CNS(=O)(=O)c2ccccc2)nn1-c1ncccc1Cl] | 2.42 | 646 | 10.45 (s, NH)<br>10.15 (s, NH)<br>3.60 and 3.51 (br, s, 3H)<br>2.90 (s, 3H) |
| 72 | 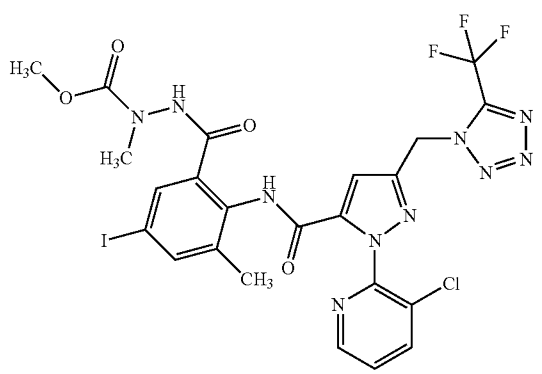 [SMILES: COC(=O)N(C)NC(=O)c1cc(I)cc(C)c1NC(=O)c1cc(Cn2nnnc2C(F)(F)F)nn1-c1ncccc1Cl] | 2.78 | 719 | 10.43 (s, NH)<br>10.19 (s, NH)<br>3.60 and 3.50 (br, s, 3H)<br>2.87 (s, 3H) |
| 73 | 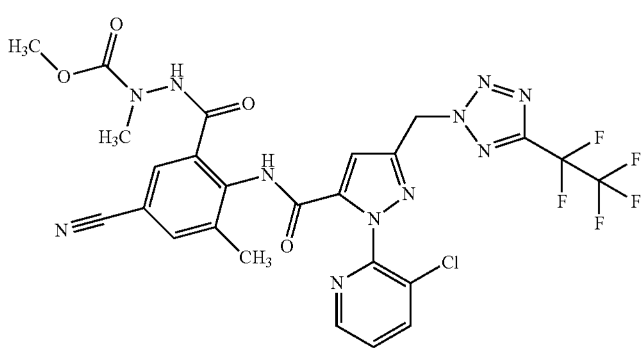 [SMILES: COC(=O)N(C)NC(=O)c1cc(C#N)cc(C)c1NC(=O)c1cc(Cn2nnc(C(F)(F)C(F)(F)F)n2)nn1-c1ncccc1Cl] | 2.97 | 668 | 10.55 (s, NH)<br>10.48 (s, NH)<br>3.60 and 3.47 (br, s, 3H)<br>2.87 (s, 3H) |

| Ex. | Structure | logP | MH+ | ¹H-NMR (400 MHz, DMSO, δ, ppm), selected signals |
|---|---|---|---|---|
| 74 | 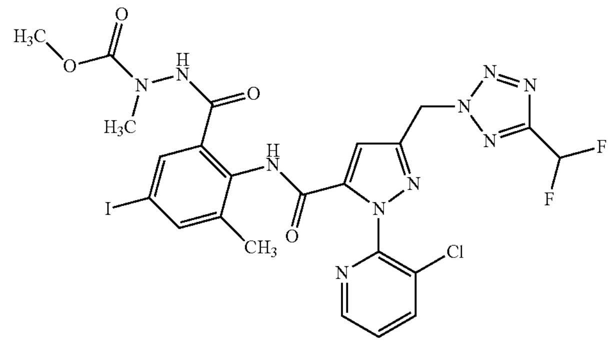 [SMILES: COC(=O)N(C)NC(=O)c1cc(I)cc(C)c1NC(=O)c1cc(Cn2nnc(C(F)F)n2)nn1-c1ncccc1Cl] | 2.64 | 701 | 10.41 (s, NH)<br>10.19 (s, NH)<br>3.64 and 3.45 (br, s, 3H)<br>2.87 (s, 3H) |
| 75 | 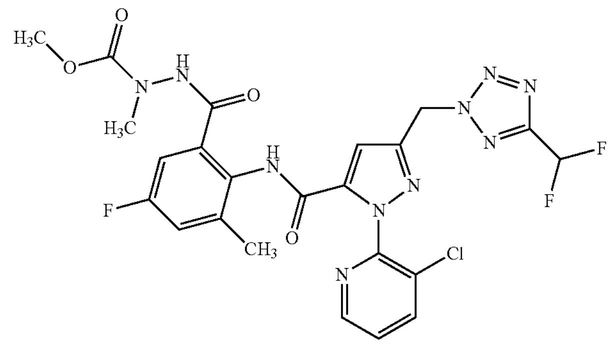 [SMILES: COC(=O)N(C)NC(=O)c1cc(F)cc(C)c1NC(=O)c1cc(Cn2nnc(C(F)F)n2)nn1-c1ncccc1Cl] | 2.19 | 593 | 10.41 (s, NH)<br>10.15 (s, NH)<br>3.66 and 3.48 (br, s, 3H)<br>2.90 (s, 3H) |
| 76 | 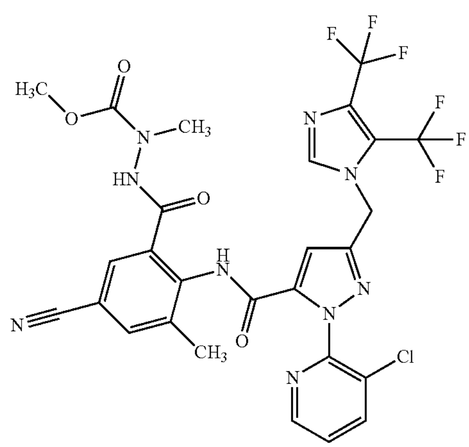 [SMILES: COC(=O)N(C)NC(=O)c1cc(C#N)cc(C)c1NC(=O)c1cc(Cn2cnc(C(F)(F)F)c2C(F)(F)F)nn1-c1ncccc1Cl] | 2.77 | 684 | 10.55 (s, NH)<br>10.42 (s, NH)<br>3.60 and 3.47 (br, s, 3H)<br>2.87 (s, 3H) |
| 77 | 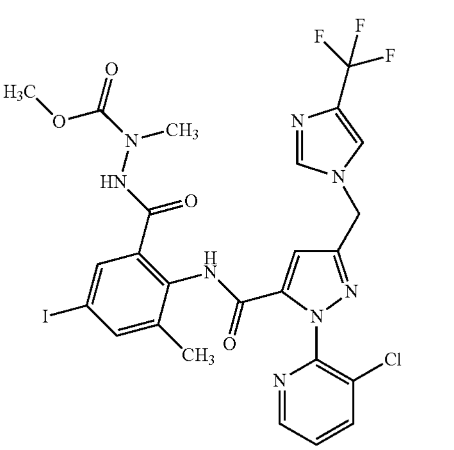 [SMILES: COC(=O)N(C)NC(=O)c1cc(I)cc(C)c1NC(=O)c1cc(Cn2cnc(C(F)(F)F)c2)nn1-c1ncccc1Cl] | 2.56 | 717 | 10.45 (s, NH)<br>10.20 (s, NH)<br>3.64 and 3.45 (br, s, 3H)<br>2.86 (s, 3H) |

-continued

| Ex. | Structure | logP | MH+ | ¹H-NMR (400 MHz, DMSO, δ, ppm), selected signals |
|---|---|---|---|---|
| 78 | 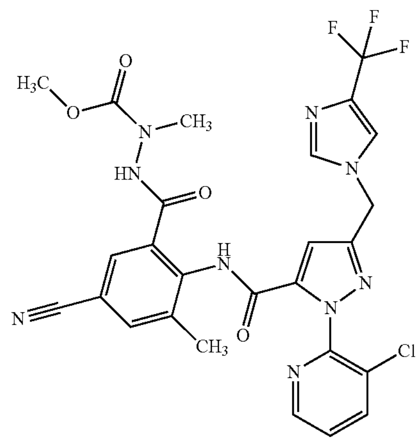 [SMILES: COC(=O)N(C)NC(=O)c1cc(C#N)cc(C)c1NC(=O)c1cc(Cn2cnc(C(F)(F)F)c2)nn1-c1ncccc1Cl] | 2.10 | 616 | NMR in CH₃CN:<br>9.40 (br, NH), 8.95 (s, NH),<br>3.65 and 3.50 (br, 3H), 3.01 (s, 3H) |
| 79 | 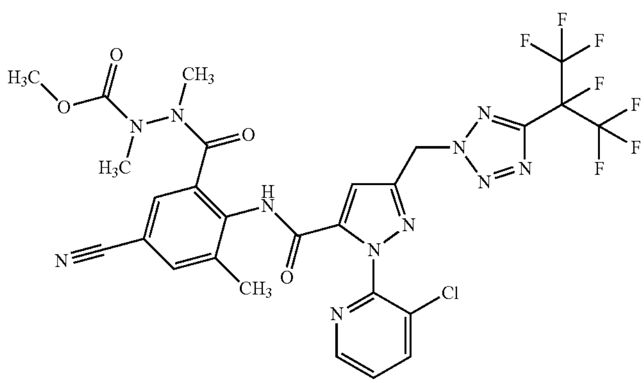 [SMILES: COC(=O)N(C)N(C)C(=O)c1cc(C#N)cc(C)c1NC(=O)c1cc(Cn2nnc(C(F)(C(F)(F)F)C(F)(F)F)n2)nn1-c1ncccc1Cl] | 3.66 | 732 | 10.62 (s, NH)<br>10.35 (s, NH)<br>3.68 and 3.58 (br, s, 3H)<br>3.06 (s, 3H) |
| 80 | 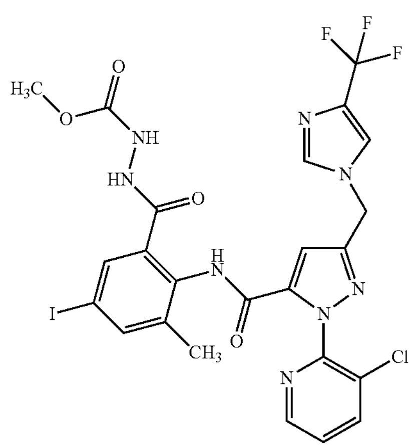 [SMILES: COC(=O)NNC(=O)c1cc(I)cc(C)c1NC(=O)c1cc(Cn2cnc(C(F)(F)F)c2)nn1-c1ncccc1Cl] | 2.38 | 703 | NMR in DMF-d₉:<br>10.34 (s, NH), 10.25 (s, NH),<br>9.33 (s, NH), 3.51 (s, 3H), 2.95 (s, 3H) |

-continued

| Ex. | Structure | logP | MH+ | ¹H-NMR (400 MHz, DMSO, δ, ppm), selected signals |
|---|---|---|---|---|
| 81 | 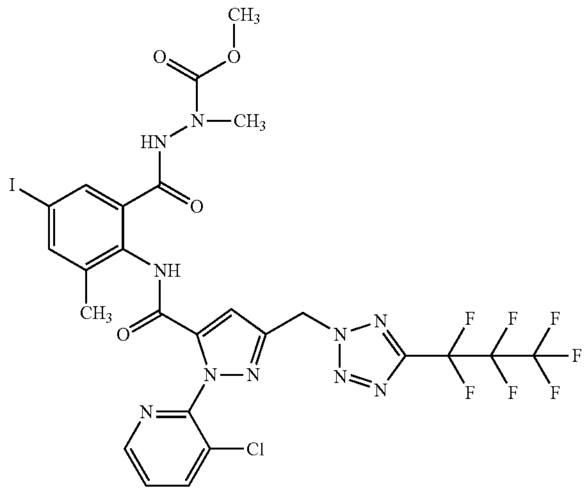 [SMILES: COC(=O)N(C)NC(=O)c1cc(I)cc(C)c1NC(=O)c1cc(Cn2nnc(C(F)(F)C(F)(F)C(F)(F)F)n2)nn1-c1ncccc1Cl] | 3.85 | | |
| 82 | 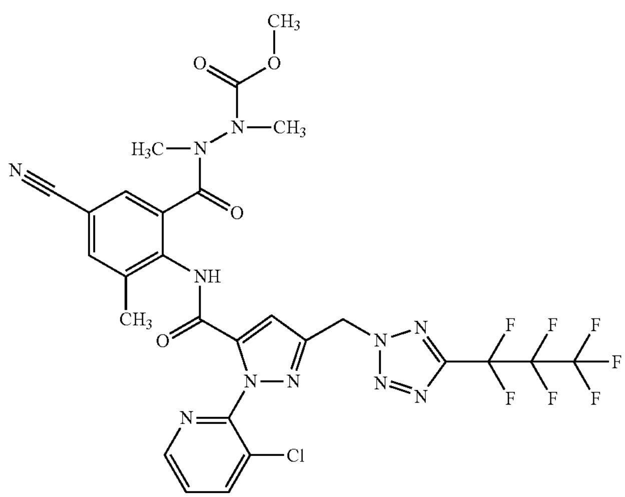 [SMILES: COC(=O)N(C)N(C)C(=O)c1cc(C#N)cc(C)c1NC(=O)c1cc(Cn2nnc(C(F)(F)C(F)(F)C(F)(F)F)n2)nn1-c1ncccc1Cl] | 3.67 | | |
| 83 | 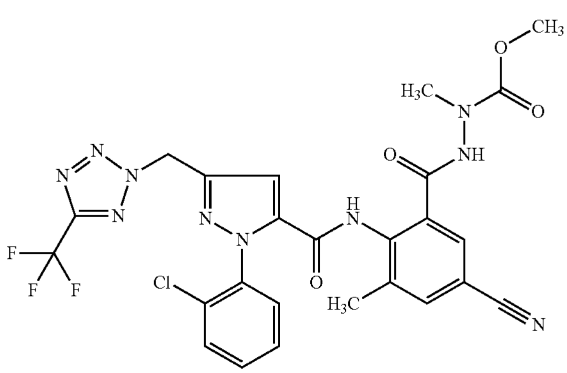 [SMILES: COC(=O)N(C)NC(=O)c1cc(C#N)cc(C)c1NC(=O)c1cc(Cn2nnc(C(F)(F)F)n2)nn1-c1ccccc1Cl] | 2.97 | 620 | 10.37 (br s, NH), 7.95 (br s, NH), 3.30 (brs, 3H), 2.84 (s, 3H) |

-continued

| Ex. | Structure | logP | MH+ | ¹H-NMR (400 MHz, DMSO, δ, ppm), selected signals |
|---|---|---|---|---|
| 84 | 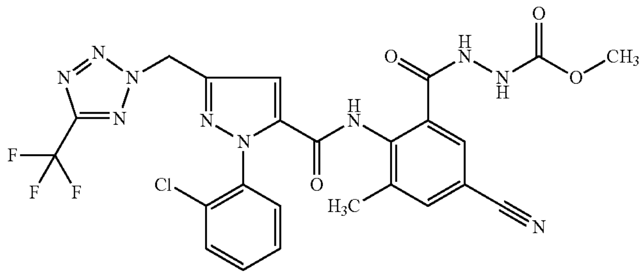 [SMILES: COC(=O)NNC(=O)c1cc(C#N)cc(C)c1NC(=O)c1cc(Cn2nnc(C(F)(F)F)n2)nn1-c1ccccc1Cl] | 2.79 | 603 | 10.22 (br s, NH), 7.94 (br, NH), 3.60 (br, 3H) |
| 85 | 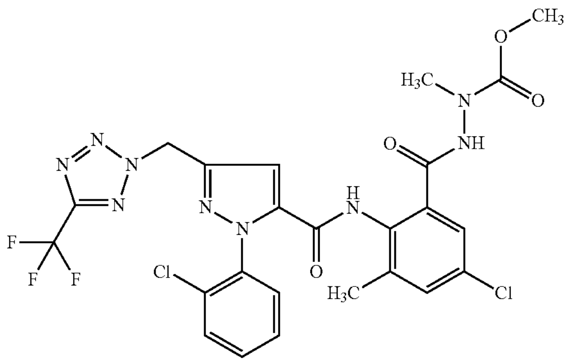 [SMILES: COC(=O)N(C)NC(=O)c1cc(Cl)cc(C)c1NC(=O)c1cc(Cn2nnc(C(F)(F)F)n2)nn1-c1ccccc1Cl] | 3.34 | 627 | 10.13 (br, NH), 7.5 (br, NH), 3.39 (br, 3H), 2.79 (s, 3H) |
| 86 | 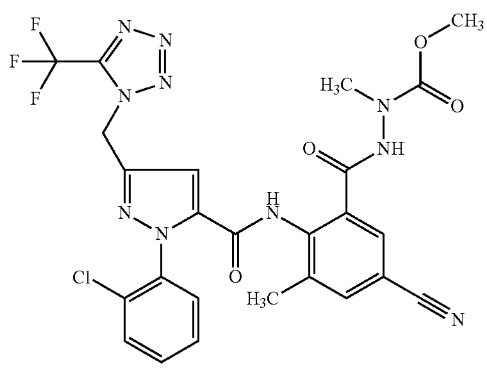 [SMILES: COC(=O)N(C)NC(=O)c1cc(C#N)cc(C)c1NC(=O)c1cc(Cn2nnnc2C(F)(F)F)nn1-c1ccccc1Cl] | 2.69 | 620 | 10.37 (br, NH), 7.94 (br, NH), 3.30 (br, 3H), 2.67 (br, 3H), |

APPLICATION EXAMPLES

Example 1

| Myzus test (MYZUPE spray treatment) | |
|---|---|
| Solvent: | 78.0 parts by weight of acetone |
| | 1.5 parts by weight of dimethylformamide |
| Emulsifier: | 0.5 part by weight of alkylaryl polyglycol ether |

An appropriate preparation of active ingredient is prepared by mixing 1 part by weight of active ingredient with the stated amounts of solvent and emulsifier and diluting the concentrate with emulsifier-containing water to the desired concentration. Leaf discs of Chinese cabbage (*Brassica pekinensis*) infested with all stages of the green peach aphid (*Myzus persicae*) are sprayed with a preparation of active ingredient at the desired concentration.

After 6 days the activity is determined, in %. Here, 100% means that all of the aphids have been killed; 0% means that no aphids have been killed.

In this test, for example, the following compounds from the Preparation Examples exhibit activity of
80% at an application rate of 100 g/ha: Ex.: 39, 65, 77, 81

In this test, for example, the following compounds from the Preparation Examples exhibit activity of
90% at an application rate of 100 g/ha: Ex.: 11, 20, 21, 32, 47, 54, 61, 78

In this test, for example, the following compounds from the Preparation Examples exhibit activity of
100% at an application rate of 100 g/ha: Ex.:
1, 3, 4, 5, 6, 7, 8, 12, 16, 17, 22, 23, 25, 26, 27, 28, 29, 30, 31, 33, 34, 35, 36, 37, 38, 41, 42, 45, 46, 48, 49, 50, 51, 52, 53 60, 63, 66, 68, 69, 72, 73, 74, 75, 79, 82, 83, 84, 85, 86

Example 2

| Phaedon test (PHAECO spray treatment) | |
|---|---|
| Solvent: | 78.0 parts by weight of acetone |
| | 1.5 parts by weight of dimethylformamide |
| Emulsifier: | 0.5 part by weight of alkylaryl polyglycol ether |

An appropriate preparation of active ingredient is prepared by mixing 1 part by weight of active ingredient with the stated amounts of solvent and emulsifier and diluting the concentrate with emulsifier-containing water to the desired concentration. Leaf discs of Chinese cabbage (*Brassica pekinensis*) are sprayed with a preparation of active ingredient at the desired concentration and, after drying, are populated with larvae of the mustard beetle (*Phaedon cochleariae*).

After 7 days, the activity is determined, in %. Here, 100% means that all the beetle larvae have been killed; 0% means that no beetle larvae have been killed.

In this test, for example, the following compounds from the Preparation Examples exhibit activity of 100% at an application rate of 100 g/ha:

Ex.:
1, 2, 3, 4, 5, 6, 7, 8, 11, 12, 13, 14, 16, 17, 19, 20, 22, 23, 25, 26, 27, 28, 29, 30, 31, 32, 33, 34, 35, 36, 37, 38, 41,
42, 45, 46, 47, 48, 49, 50, 51, 52, 53, 54, 59, 60, 61, 63, 66, 68, 69, 72, 73, 74, 75, 79, 81, 82, 83, 84, 85, 86

Example 3

| *Spodoptera frugiperda* test (SPODFR spray treatment) | |
|---|---|
| Solvent: | 78.0 parts by weight of acetone |
| | 1.5 parts by weight of dimethylformamide |
| Emulsifier: | 0.5 part by weight of alkylaryl polyglycol ether |

An appropriate preparation of active ingredient is prepared by mixing 1 part by weight of active ingredient with the stated amounts of solvent and emulsifier and diluting the concentrate with emulsifier-containing water to the desired concentration. Leaf discs of maize (*Zea mays*) are sprayed with a preparation of active ingredient at the desired concentration and, after drying, are populated with caterpillars of the army worm (*Spodoptera frugiperda*).

After 7 days, the activity is determined, in %. Here, 100% means that all the caterpillars have been killed; 0% means that no caterpillar has been killed.

In this test, for example, the following compound from the Preparation Examples exhibits activity of 83% at an application rate of 100 g/ha: Ex.: 77

In this test, for example, the following compound from the Preparation Examples exhibits activity of 100% at an application rate of 100 g/ha:

Ex.:
1, 2, 3, 4, 5, 6, 7, 8, 11, 12, 13, 14, 15, 16, 17, 19, 20, 21, 23, 25, 26, 27, 28, 29, 30, 31, 32, 33, 34, 35, 36, 37, 38,
41, 42, 45, 46, 47, 48, 49, 50, 51, 52, 53, 54, 59, 60, 61, 62, 63, 65, 66, 68, 69, 72, 73, 74, 75, 79, 81, 82, 83, 84, 85, 86

Example 4

| *Tetranychus* test, OP-resistant (TETRUR spray treatment) | |
|---|---|
| Solvent: | 78.0 parts by weight of acetone |
| | 1.5 parts by weight of dimethylformamide |
| Emulsifier: | 0.5 part by weight of alkylaryl polyglycol ether |

An appropriate preparation of active ingredient is prepared by mixing 1 part by weight of active ingredient with the stated amounts of solvent and emulsifier and diluting the concentrate with emulsifier-containing water to the desired concentration. Leaf discs of bean (*Phaseolus vulgaris*) infested with all stages of the greenhouse red spidermite (*Tetranychus urticae*) are sprayed with a preparation of active ingredient at the desired concentration. After 6 days the activity is determined, in %. Here, 100% means that all of the mites have been killed; 0% means that no mites have been killed.

In this test, for example, the following compound from the Preparation Examples exhibits activity of 90% at an application rate of 100 g/ha: 83

In this test, for example, the following compound from the Preparation Examples exhibits activity of 100% at an application rate of 100 g/ha: 59

In this test, for example, the following compound from the Preparation Examples exhibits activity of 100% at an application rate of 500 g/ha: 67.

Analytical Methods

The logP values reported in the table above and in the Preparation Examples were determined in accordance with EEC Directive 79/831 Annex V.A8 by HPLC (High Performance Liquid Chromatography) on reversed-phase columns (C 18), with the following methods:

[a] The determination is made in the acid range at pH 2.3 with 0.1% aqueous phosphoric acid and acetonitrile as eluents; linear gradient from 10% acetonitrile to 95% acetonitrile.

[b] The determination is made by LC-MS in the acid range at pH 2.7 with 0.1% aqueous formic acid and acetonitrile (containing 0.1% formic acid) as eluents; linear gradient from 10% acetonitrile to 95% acetoneitrile.

Calibration took place with unbranched alkan-2-ones (having 3 to 16 carbon atoms) of known logP values (logP values determined from the retention times, by linear interpolation between two successive alkanones).

The lambda-maX values were determined on the basis of the UV spectra from 200 nm to 400 nm in the maxima of the chromatographic signals.

The MH$^+$ signals were determined using an Agilent MSD system with ESI and positive or negative ionization.

The NMR spectra were a) determined with a Bruker Avance 400 equipped with a flow sample head (60 µl volume). Solvents used were $CD_3CN$ or $d_6$-DMSO, and tetramethylsilane (0.00 ppm) was used as reference.

b) determined with a Bruker Avance II 600. Solvents used were $CD_3CN$ or $d_6$-DMSO, with tetramethylsilane (0.00 ppm) used as reference.

The splitting of the signals was described as follows: s (singlet), d (doublet), t (triplet), q (quartet), quin (quintet), m (multiplet).

The invention claimed is:
1. An anthranilic acid derivative of general formula (I)

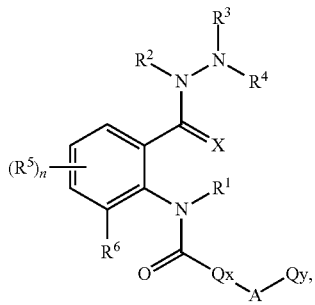

in which
- $R^1$ is hydrogen, amino, or hydroxyl or is $C_1$-$C_6$-alkyl, $C_2$-$C_6$-alkenyl, $C_2$-$C_6$-alkynyl or $C_3$-$C_6$-cycloalkyl, each of which is optionally substituted one or more times by identical or different substituents, the substituents being selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, $(C_1$-$C_4$-alkoxy)carbonyl, $C_1$-$C_4$-alkylamino, di($C_1$-$C_4$-alkyl)amino, $C_3$-$C_6$-cycloalkylamino, or $(C_1$-$C_4$-alkyl)$C_3$-$C_6$-cycloalkylamino,
- $R^2$, $R^3$ independently of one another are hydrogen, $C_2$-$C_6$-alkoxycarbonyl, $C_2$-$C_6$-alkylcarbonyl, $C_2$-$C_6$-alkylaminocarbonyl, or $C_2$-$C_6$-dialkylaminocarbonyl or are $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, or $C_3$-$C_6$-trialkylsilyl, or
- $R^2$ and $R^3$ independently of one another are a phenyl ring or a 5- or 6-membered unsaturated, partially saturated or saturated heterocycle, the phenyl ring or the heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, (C=O)NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkyl sulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, $(C_1$-$C_6$-alkyl)carbonyl, $(C_1$-$C_6$-alkoxy)carbonyl, $(C_1$-$C_6$-alkyl)aminocarbonyl, di($C_1$-$C_4$-alkyl)aminocarbonyl, tri($C_1$-$C_2$)alkylsilyl, or $(C_1$-$C_4$-alkyl)$(C_1$-$C_4$-alkoxy)imino, or
- $R^2$ and $R^3$ are joined to one another via two to six carbon atoms and form a ring which optionally additionally contains a nitrogen, sulphur or oxygen atom and may optionally be substituted one to four times by $C_1$-$C_2$-alkyl, $C_1$-$C_2$-haloalkyl, halogen, cyano, amino, $C_1$-$C_2$-alkoxy, or $C_1$-$C_2$-haloalkoxy,
- $R^4$ is a group selected from —C(=S)—$R^8$, —C(=O)—$R^8$, —C(=O)—O$R^9$, —C(=S)—O$R^9$, —C(=O)—S$R^{10}$, —C(=S)—S$R^{10}$, —(=O)—N$R^{11}R^{12}$, —C(=S)—N$R^{11}R^{12}$, —S(O)$_2$—$R^{13}$, or —S(O)$_2$—N$R^{14}R^{15}$,
- or $R^3$ and $R^4$ together are =C$R^{16}$ if $R^2$ and $R^3$ are not joined to one another via two to six carbon atoms and do not form a ring,
- $R^5$ is hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, SF$_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, $(C_1$-$C_4$-alkoxy)imino, $(C_1$-$C_4$-alkyl)$(C_1$-$C_4$-alkoxy)imino, $(C_1$-$C_4$-haloalkyl)$(C_1$-$C_4$-alkoxy)imino, or $C_3$-$C_6$-trialkylsilyl, or
- two radicals $R^5$ form, via adjacent carbon atoms, a ring which is —(CH$_2$)$_3$—, —(CH$_2$)$_4$—, —(CH$_2$)$_5$—, —(CH—CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)—, or —(CH=CH—N=CH)—, or
- two radicals $R^5$, form via adjacent carbon atoms the fused rings below, which are optionally substituted one or more times by identical or different substituents, the substituents being selectable independently of one another from hydrogen, cyano, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino, or $C_3$-$C_6$-cycloalkylamino, or

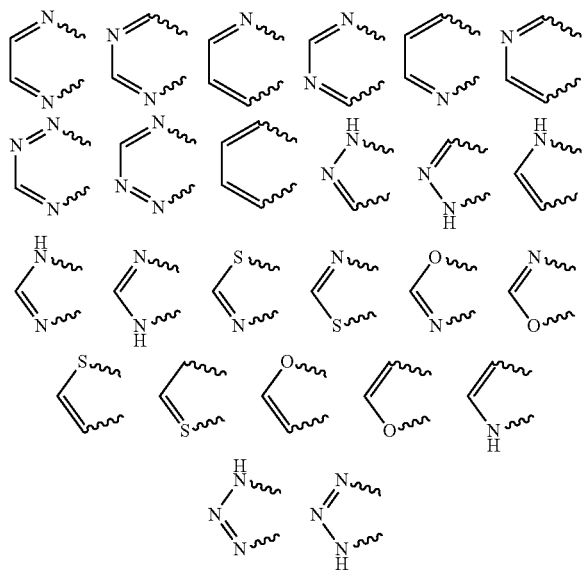

n is 0 to 3,
X is O or S,
$R^6$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_{1-4}$-sulphinyl, $C_1$-$C_4$-alkylsulphony, $C_1$-$C_4$-haloalkylthio, $C_1$-$C_4$-haloalkylsulphinyl, $C_1$-$C_4$-haloalkylsulphonyl, halogen, cyano, nitro, or $C_3$-$C_6$-trialkylsilyl, $Q_X$ is a heteroaromatic 5- or 6-membered ring which is substituted one or more times by identical or different substituents $R^7$ and which may contain 1-3 heteroatoms from N, S, or O, A is optionally singly or multiply substituted —($C_1$-$C_6$-alkylene)-, —($C_1$-$C_6$-alkenylene)-, —($C_1$-$C_6$-alkynylene)-, —$R^{17}$—($C_3$-$C_6$-cycloalkyl)-$R^{17}$—, —$R^{17}$—O—$R^{17}$—, —$R^{17}$—S—$R^{17}$—, —$R^{17}$—S(=O)—$R^{17}$, —$R^{17}$—S(=O)$_2$—$R^{17}$—, —$R^{17}$—NH—($C_1$-$C_6$-alkyl)-, —$R^{17}$—N($C_1$-$C_6$-alkyl)-$R^{17}$—, —$R^{17}$—C=NO($C_1$-$C_6$-alkyl)-, —CHCO$_2$($C_1$-$C_6$-alkyl)-, —$R^{17}$—C(=O)—$R^{17}$—, —$R^{17}$—C(O)NH—$R^{17}$—, —$R^{17}$—C(=O)N($C_1$-$C_6$-alkyl)-$R^{17}$, —$R^{17}$—C(=O)NHNH—$R^{17}$—, —$R^{17}$—C(=O)N($C_1$-$C_6$-alkyl)-NH—$R^{17}$—, —$R^{17}$—C(=O)NHN($C_1$-$C_6$-alkyl)-$R^{17}$—, —$R^{17}$—O(C=O)—$R^{17}$—, —$R^{17}$—O(C=O)NH—$R^{17}$—, —$R^{17}$—O(C=O)N($C_1$-$C_6$-alkyl)-$R^{17}$—, —$R^{17}$—S(=O)$_2$NH—$R^{17}$, —$R^{17}$—S(=O)$_2$N($C_1$-$C_6$-alkyl)-$R^{17}$—, —$R^{17}$—S(C=O)—$R^{17}$—, —$R^{17}$—S(C=O)NH—$R^{17}$—, —$R^{17}$—S(=O)N($C_1$-$C_6$-alkyl)-$R^{17}$—, —$R^{17}$—NHNH—$R^{17}$—, —$R^{17}$—NHN($C_1$-$C_6$-alkyl)-$R^{17}$—, —$R^{17}$—N($C_1$-$C_6$-alkyl)-NH—$R^{17}$—, —$R^{17}$—N($C_1$-$C_6$-alkyl)-N($C_1$-$C_6$-alkyl)-$R^{17}$—, —$R^{17}$—N=CH—O—$R^{17}$—, —$R^{17}$—NH(C=O)O—$R^{17}$—, —$R^{17}$—N($C_1$-$C_6$-alkyl)-(C=O)O—$R^{17}$—, —$R^{17}$—NH(C=O)NH—$R^{17}$—, —$R^{17}$—NH(C=S)NH—$R^{17}$—, —$R^{17}$—NHS(=O)$_2$—$R^{17}$—, or —$R^{17}$—N($C_1$-$C_6$-alkyl)S(=O)$_2$—$R^{17}$—, the substituents being selectable independently of one another from halogen, cyano, nitro, hydroxyl, $C_1$-$C_6$-alkyl, $C_1$-$C_6$-alkoxy, or halo-$C_1$-$C_6$-alkyl, where —($C_3$-$C_6$-cycloalkyl)- in the ring may optionally contain 1 to 2 heteroatoms selected from N, S, or O, $R^{17}$ is linear or branched —($C_1$-$C_6$-alkylene)- or is a direct bond, or two or more radicals $R^{17}$ independently of one another are linear or branched —($C_1$-$C_6$-alkylene)-, or are a direct bond, $Q^Y$ is a 5- or 6-membered, partially saturated or saturated heterocyclic or heteroaromatic ring or an aromatic 8-, 9- or 10-membered fused heterobicyclic ring system or is phenyl, the ring or ring system being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, CO$_2$H, CO$_2$NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, or the substituents being selectable independently of one another from phenyl or a 5- or 6-membered heteroaromatic ring, where phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, NO$_2$, OH, $C_1$-$C_4$-alkoxy, or $C_1$-$C_4$-haloalkoxy substituents, $R^7$ is $C_3$-$C_6$-cycloalkyl or

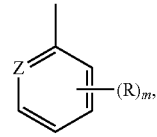

R independently at each occurrence is hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-haloalkylthio, $C_1$-$C_4$-haloalkylsulphonyl, or ($C_1$-$C_4$-alkyl)$C_1$-$C_4$-alkoxyimino, m is 0 to 4, Z is N, CH, CF, CCl, CBr or CI, $R^8$ is hydrogen or is $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di($C_1$-$C_4$-alkyl)amino, $C_3$-$C_6$-cycloalkylamino, a phenyl ring or a 3- to 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkylamino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, or $R^8$ is a phenyl ring or a 3- to 6-membered unsaturated, partially saturated or saturated heterocycle, the heteroatoms being selected from N, S, or O, where the phenyl ring or heterocycle is optionally substituted one or more times by identical or different substituents, and where the substituents are selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, CONH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphony $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)

amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, $R^9$, $R^{10}$, $R^{13}$, $R^{14}$ and $R^{15}$ independently of one another are $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally substituted one or more times by identical or different substituents, the substituents being selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di($C_1$-$C_4$-alkyl)amino, $C_3$-$C_6$-cycloalkylamino, a phenyl ring or a 3- or 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl or ($C_1$-$C_4$-alkyl)($C_1$-$C_4$-alkoxy)imino, or $R^9$, $R^{10}$, $R^{13}$, $R^{14}$ and $R^{15}$ independently of one another are a phenyl ring or are a 3- to 6-membered unsaturated, partially saturated or saturated heterocycle, the heteroatoms being selected from N, S, or O, the phenyl ring or heterocycle being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkylsilyl, or ($C_1$-$C_4$-alkyl)($C_1$-$C_4$-alkoxy)imino, $R^{11}$ and $R^{12}$ independently of one another are hydrogen or are $R^9$, $R^{16}$ is a phenyl ring or is a 5- or 6-membered heteroaromatic ring, the heteroatoms being selected from the series N, S, or O, the ring being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$)alkyl or ($C_1$-$C_4$-alkyl)($C_1$-$C_4$-alkoxy)imino, and N-oxides and salts thereof.

2. The anthranilic acid derivative of general formula (I) according to claim 1, in which $R^1$ is hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl, or $C_1$-$C_4$-alkylsulphonyl-$C_1$-$C_4$-alkyl, $R^2$ and $R^3$ independently of one another are hydrogen or are $C_1$-$C_6$-alkyl or $C_3$-$C_6$-cycloalkyl optionally substituted one or more times by identical or different substituents, the substituents being selectable independently of one another from halogen, cyano, $C_2$-$C_6$-alkoxycarbonyl, or $C_2$-$C_6$-alkylcarbonyl, $R^4$ is —C(=O)—$R^8$, —C(=O)—$OR^9$, —C(=O)—$SR^{10}$, —C(=O)—$NR^{11}R^{12}$, —S(O)$_2$—$R^{13}$, or —S(O)$_2$—$NR^{14}R^{15}$, $R^5$ is hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio, or $C_1$-$C_4$-haloalkylthio, or two adjacent radicals $R^5$ are —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)—, or —(CH=CH—N=CH)—, n is 0 to 2, X is O or S, $R^6$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro, or $C_3$-$C_6$-trialkylsilyl, $Q^X$ is a heteroaromatic 5-membered ring which is substituted one or more times by identical or different substituents $R^7$ and which may contain 1-3 heteroatoms from N, O, or S, or is a heteroaromatic 6-membered ring which is substituted one or more times by identical or different substituents $R^7$ and which may contain 1-3 nitrogen atoms, A is optionally singly or multiply substituted —($C_1$-$C_4$-alkylene)-, —($C_1$-$C_4$-alkenylene)-, —($C_1$-$C_4$-alkynylene)-, —$R^{17}$—($C_3$-$C_6$-cycloalkyl)-$R^{17}$—, —$R^{17}$—, —$R^{17}$—S—$R^{17}$—, —$R^{17}$—S(—O)—$R^{17}$—, —$R^{17}$—S(=O)$_2$—$R^{17}$—, —$R^{17}$—NH—($C_1$-$C_4$-alkyl)-, —$R^{17}$—N($C_1$-$C_4$-alkyl)-$R^{17}$—, —$R^{17}$—C=NO($C_1$-$C_4$-alkyl)-, —$R^{17}$—C(=O)—$R^{17}$—, —$R^{17}$—C(=S)—$R^{17}$, —$R^{17}$—C(=O)NH—$R^{17}$—, —$R^{17}$—C(=O)N($C_1$-$C_4$-alkyl)-$R^{17}$—, —$R^{17}$—S(=O)$_2$NH—$R^{17}$—, —$R^{17}$—S(=O)$_2$N($C_1$-$C_4$-alkyl)-$R^{17}$—, —$R^{17}$—NH(C=O)O—$R^{17}$—, —$R^{17}$—N($C_1$-$C_4$-alkyl)-(C=O)O—$R^{17}$—, —$R^{17}$—NH(C=O)NH—$R^{17}$—, —$R^{17}$—NHS(=O)$_2$—$R^{17}$—, or —$R^{17}$—N($C_1$-$C_4$-alkyl)S(=O)$_2$—$R^{17}$—, the substituents being selectable independently of one another from halogen, cyano, nitro, hydroxyl, $C_1$-$C_6$-alkyl, $C_1$-$C_6$-alkoxy, or halo-$C_1$-$C_6$-alkyl, $R^7$ is the radical

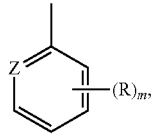

or $R^7$ is $C_3$-$C_6$-cycloalkoxy,

R independently at each occurrence is hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl, or ($C_1$-$C_4$-alkyl)$C_1$-$C_4$-alkoxyimino, m is 1, 2 or 3, $R^8$ is hydrogen or singly or multiply identically or differently substituted $C_1$-$C_6$-alkyl or $C_3$-$C_6$-cycloalkyl, the substituents being selectable independently of one another from halogen, cyano, a phenyl ring or a 3- or 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy, or $C_1$-$C_4$-haloalkoxy, or $R^8$ is a phenyl ring or is a 3- to 6-membered unsaturated, partially saturated or saturated heterocycle, the heteroatoms being selected from N, S, or O, and the phenyl ring or heterocycle being optionally substituted one or more times by identical or different substituents, and the substituents being selectable independently of one another from hydrogen, $C_1$-$C_6$-haloalkyl, halogen, or cyano, Z is N, CH, CF, CCl, CBr, or CI, $R^9$, $R^{10}$, $RR^{13}$, $R^{14}$ and $R^{15}$ independently of one another are singly or multiply identically or differently substituted $C_1$-$C_6$-alkyl or $C_3$-$C_6$-cycloalkyl, the substituents being selectable independently of one another from halogen, cyano, a phenyl ring or a 3- to 6-membered unsaturated, partially saturated or saturated heterocycle, the phenyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy, or $C_1$-$C_4$-haloalkoxy, or $R^9$, $R^{10}$, $R^{13}$, $R^{14}$, and $R^{15}$ independently of one another are a phenyl ring or are a 3- to 6-membered unsaturated, partially saturated or saturated heterocycle, the heteroatoms being selected from N, S and O, the phenyl ring or the heterocycle being optionally substituted one or more times by identical or different substituents, and the substituents being selectable independently of one another from hydrogen, $C_1$-$C_6$-alkyl, $C_1$-$C_6$-haloalkyl, halogen, or cyano, $R^{11}$ and $R^{12}$ independently of one another are hydrogen or are $R^9$, $R^{16}$ is a phenyl ring or is a 5- or 6-membered heteroaromatic frig where the heteroatoms are selected from N, S, or O, the ring being optionally substituted one or more times by identical or different substituents, and the substituents being selectable independently of one another from hydrogen, $C_1$-$C_6$-alkyl, $C_1$-$C_6$-haloalkyl, halogen, cyano, $NO_2$, $C_1$-$C_4$-alkoxy, or $C_1$-$C_4$-haloalkoxy, $R^{17}$ is linear or branched —($C_1$-$C_4$-alkylene)- or is a direct bond, $Q_Y$ is a 5- or 6-membered, partially saturated or a saturated heterocyclic or heteroaromatic ring or an aromatic 8-, 9- or 10-membered fused heterobicyclic ring system, the heteroatoms being selectable from N, S, or O, the ring or the ring system being optionally substituted one or more times by identical or different substituents, and the substituents being selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_3$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, or $C_1$-$C_4$-haloalkylsulphonyl, or the substituents being selectable independently of one another from phenyl or a 5- or 6-membered heteroaromatic ring, where the phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, or $C_1$-$C_4$-haloalkoxy substituents.

3. The anthranilic acid derivative of general formula (I) according to either of claim 1 or 2, in which $R^1$ is hydrogen, methyl, ethyl, cyclopropyl, cyanomethyl, methoxymethyl, methylthiomethyl, methylsulphinylmethyl, or methylsulphonylmethyl, $R^2$ and $R^3$ independently of one another are hydrogen, methyl ethyl, isopropyl, or tert-butyl, $R^4$ is —C(=O)—$R^8$ or —C(=O)—$OR^9$, $R^5$ is hydrogen, $C_1$-$C_4$-alkyl, $C_1$-$C_2$-haloalkyl, halogen, cyano, or $C_1$-$C_2$-haloalkoxy, or two adjacent radicals $R^5$ are —$(CH_2)_4$—, —(CH=CH—)$_2$—, —$O(C_{1-12})_2O$—, —$O(CF_2)_2O$—, —(CH=CH—CH=N)— or —(CH=CH—N=CH)—, n is 1 or 2, X is O, $R^6$ is $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluoro, chloro, bromo, iodo, cyano, nitro, or $C_3$-$C_6$-trialkylsilyl, $Q_X$ is a heteroaromatic 5- or 6-membered ring which is substituted one or more times by identical or different substituents $R^7$ and is selected from the group consisting of furan, thiophene, pyrazole, triazole, imidazole, thiazole, oxazole, isoxazole, isothiazole, thiadiazole, oxadiazole, pyrrole, pyridine, pyrimidine, pyridazine and pyrazine, A is —$CH_2$—, —$CH_2O$—, —$CH_2OCH_2$—, —$CH_2S$—, —$CH_2SCH_2$—, —$CH_2N(C_1$-$C_4$-alkyl)-, —$CH_2N(C_1$-$C_4$-alkyl)$CH_2$—, —CH(Hal)-, —C(halo)$_2$-, —CH(CN)—, —$CH_2(CO)$—, —$CH_2(CS)$—, —$CH_2CH(OH)$—, -cyclopropyl-, —$CH_2(CO)CH_2$—, —CH($C_1$-$C_4$-alkyl)-, —C(Di—$C_1$-$C_6$-alkyl)-, —$CH_2CH_2$—, —CH=CH—, or —C=NO($C_1$-$C_6$-alkyl)-, $R^7$ is the radical

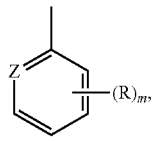

R independently at each occurrence is hydrogen, halogen, cyano, or $C_1$-$C_4$-haloalkyl,
m is 1 or 2,
Z is N, CH, CF, CCl, or CBr,
$R^8$ is hydrogen, or is methyl, ethyl, isopropyl or tert-butyl optionally singly or multiply identically or differently substituted, the substituents being selectable independently of one another from halogen, cyano, phenyl or pyridyl, where the phenyl or pyridyl is optionally substituted one or more times by identical or different hydrogen, trifluoromethyl, cyano, fluoro, chloro, bromo, or trifluoromethoxy substituents, or
$R^8$ is phenyl, or pyridyl or is a 3- to 6-membered saturated heterocycle, containing 1-2 heteroatoms from N, S, or O, the phenyl or pyridyl ring or heterocycle being optionally substituted one or more times by identical or different substituents, and the substituents being selectable independently of one another from hydrogen, $C_1$-$C_6$-alkyl, $C_1$-$C_6$-haloalkyl, halogen, or cyano,
$R^9$, $R^{10}$, $R^{13}$, $R^{14}$ and $R^{15}$ independently of one another are optionally singly or multiply identically or differently substituted methyl, ethyl, isopropyl or tert-butyl, the substituents being selectable independently of one another from halogen, cyano, phenyl or pyridyl, where phenyl or pyridyl is optionally substituted by one or more identical or different trifluoromethyl, cyano, fluoro, chloro, or trifluoromethoxy substituents, or
$R^9$, $R^{10}$, $R^{13}$, $R^{14}$ and $R^{15}$ independently of one another are phenyl, pyridyl or are a 3- to 6-membered saturated heterocycle containing 1-2 heteroatoms from N, S, or O, the phenyl or pyridinyl ring or the heterocycle being optionally substituted one or more times by identical or different substituents, and the substituents being selectable independently of one another from hydrogen, $C_1$-$C_6$-alkyl, $C_1$-$C_6$-haloalkyl, halogen, or cyano,
$R^{11}$ and $R^{12}$ independently of one another are hydrogen or are $R^9$,
$R^{16}$ is phenyl, pyridyl, pyrimidinyl, furan, or thiophene which is optionally substituted by one or more identical or different substituents, the substituents being selectable independently of one another from hydrogen, trifluoromethyl, cyano, fluoro, chloro, or trifluoromethoxy,
$R^{17}$ is methylene, ethylene, propylene, isopropylene, n-butylene, sec-butylene, isobutylene, or a direct bond,
$Q^Y$ is an optionally singly or multiply identically or differently substituted 5- or 6-membered heteroaromatic ring from the series Q-1 to Q-53, Q-58 to Q-59, or Q-62 to Q-63, or an aromatic 9-membered fused heterobicyclic ring system Q-54 to Q-56, or a 5-membered heterocyclic ring Q-60 or Q-61, the substituents being selectable independently of one another from $C_1$-$C_4$-alkyl, $C_1$-$C_3$-haloalkyl, $C_1$-$C_2$-alkoxy, halogen, cyano, hydroxyl, nitro, or $C_1$-$C_2$-haloalkoxy,
or the substituents being selectable independently of one another from phenyl or a 5- or 6-membered heteroaromatic ring, where the phenyl or the ring may optionally be substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-haloeycloalkyl, halogen, CN, $NO_2$, OH, $C_1$-$C_4$-alkoxy, or $C_1$-$C_4$-haloalkoxy substituents

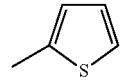
Q-1

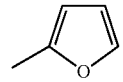
Q-2

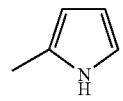
Q-3

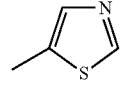
Q-4

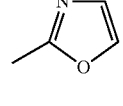
Q-5

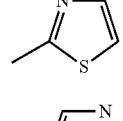
Q-6

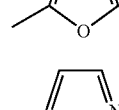
Q-7

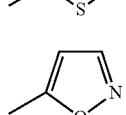
Q-8

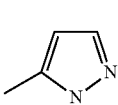
Q-9

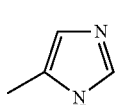
Q-10

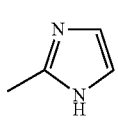
Q-11

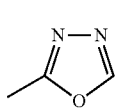
Q-12

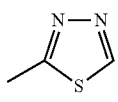
Q-13

Q-14

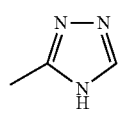 Q-15
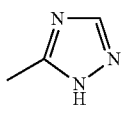 Q-16
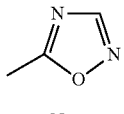 Q-17
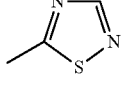 Q-18
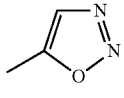 Q-19
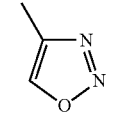 Q-20
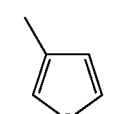 Q-21
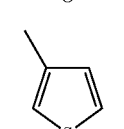 Q-22
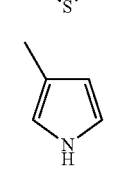 Q-23
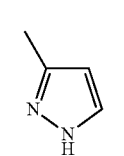 Q-24
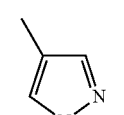 Q-25
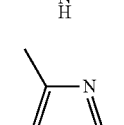 Q-26
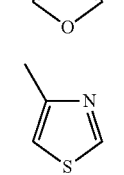 Q-27
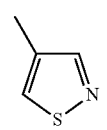 Q-28
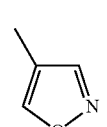 Q-29
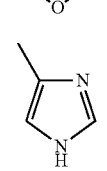 Q-30
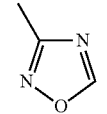 Q-31
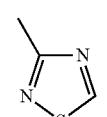 Q-32
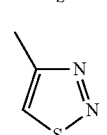 Q-33
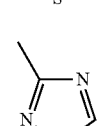 Q-34
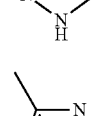 Q-35
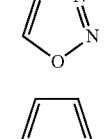 Q-36
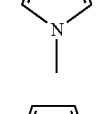 Q-37
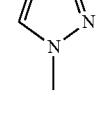 Q-38
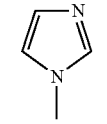 Q-39
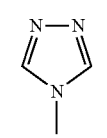

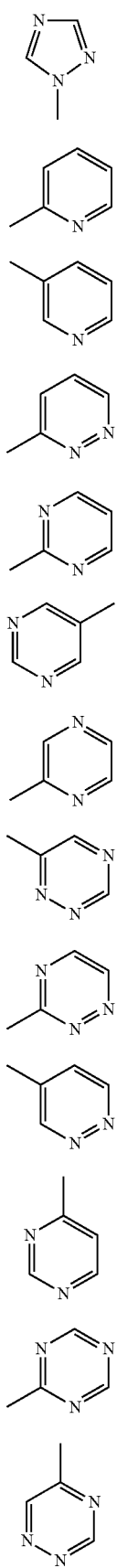
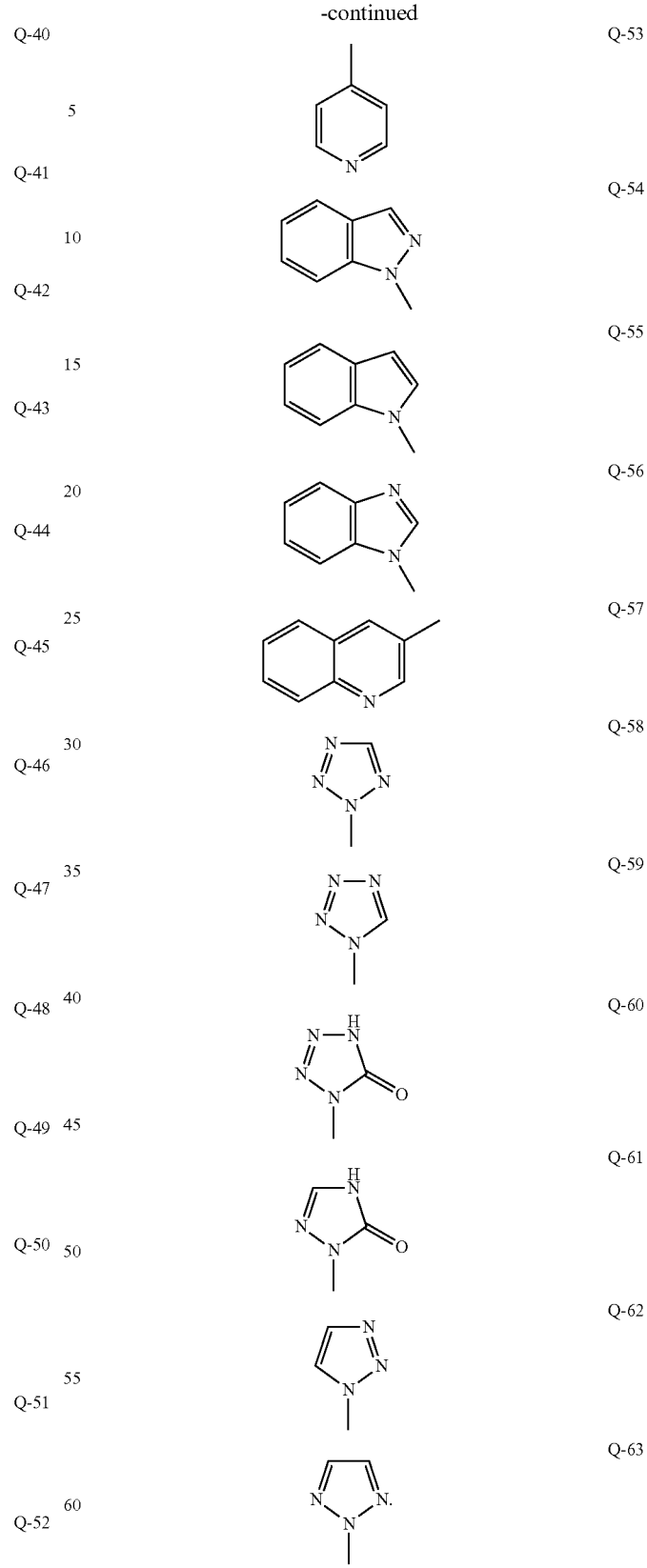
4. A mixture comprising at least two compounds of the general formula (I) according to claim 3, in which Qy of at least a first compound is Q62, and Qy of at least a second compound is Q63, and wherein the ratio of said at least first compound to said at least second compound being 60:40 to 99:1.

5. A mixture comprising at least two compounds of the general formula (I) according to claim 3, in which Qy of at least a first compound is Q58, and Qy of at least a second compounds is Q59, and wherein the ratio of said at least first compound to said at least second compound being 60:40 to 99:1.

6. A compound of general formula (VII),

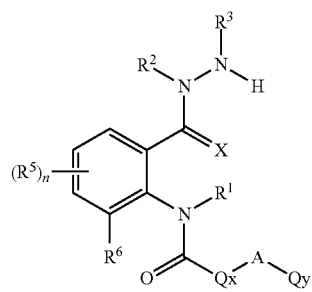

(VII)

in which $R^1$, $R^2$, $R^3$, $R^5$, $R^6$, n, Qx, A and Qy are as defined in claim 1.

7. An agrochemical composition comprising at least one compound of formula (I) according to claim 1 or the mixture of compounds of formula (I) according to claim 5 or claim 6, and one or more extenders and/or one or more surface-active substances.

8. A process for producing an agrochemical composition comprising mixing at least one compound of the general formula (I) according to claim 1 or mixing the mixture of compounds of the general formula (I) according to claim 5 or claim 6 with one or more extenders and/or one or more surface-active substances.

9. An anthranilic acid derivative having the following structural formula:

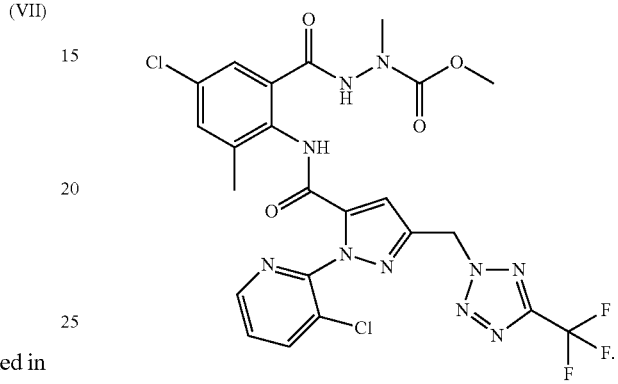

* * * * *